United States Patent [19]
Williams et al.

[11] Patent Number: 5,460,810
[45] Date of Patent: Oct. 24, 1995

[54] METHOD FOR MAINTAINING GUT EPITHELIAL CELLS BY TREATMENT WITH A CYTOKINE SUCH AS INTERLEUKIN 11

[75] Inventors: David A. Williams, Indianapolis, Ind.; Steven C. Clark, Winchester, Mass.

[73] Assignee: Genetics Institute, Inc., Cambridge, Mass.

[21] Appl. No.: 941,372

[22] Filed: Sep. 2, 1992

[51] Int. Cl.⁶ .......................... A61K 38/18; A61K 38/19; A61K 38/20
[52] U.S. Cl. .......................... 424/85.1; 424/85.2; 514/867; 514/908
[58] Field of Search ............................... 514/2, 880, 893, 514/917, 925; 424/85.1, 85.2

[56] References Cited

U.S. PATENT DOCUMENTS

| | | | |
|---|---|---|---|
| 5,082,658 | 1/1992 | Palladino | 424/85.2 |
| 5,215,895 | 6/1993 | Bennett et al. | 435/69.52 |

OTHER PUBLICATIONS

Bruce et al., Prog. Growth Factor Res, 4:157–170 (1992).
Ip et al., Cell 63:1121–1132 (1992).
Hird et al., in: *Genes and Cancer*, Carney et al. (Eds.), John Wiley & Sons, New York, 1990, pp. 183–189.
Stedman's Medical Dictionary, Williams & Wilkins, Baltimore, Md., 1990, p. 396.
Balkwill, F. R. et al.; Immunol. Today 10:299–304 (1989).
Clark, S. C. et al.; Science 236:1229–1237 (1987).
Takatsuki, F. et al.; Cancer Res. 50:2885–2890 (1990).
Paul, S. R. et al.; Proc. Natl. Acad. Sci. USA 87:7512–7516 (1990).
Du, X. X. et al.; Blood 81:27–34 (1993).

*Primary Examiner*—Robert A. Wax
*Assistant Examiner*—Eric Grimes
*Attorney, Agent, or Firm*—M. C. Meinert; Thomas J. DesRosier; Mary E. Bak

[57] ABSTRACT

A method for reducing damage or depletion of gut epithelial cells (e.g., as a result of radiation therapy or chemotherapy) by administration of one or more of the following cytokines: interleukin 11 (IL-11), interleukin 6 (IL-6), leukemia inhibitory factor/cholinergic differentiation factor (LIF/CDF), oncostatin M (OSM), or ciliary neurotrophic factor (CNTF).

12 Claims, 7 Drawing Sheets

FIGURE 1

Human IL-11 nucleotide sequence [SEQ ID NO: 1]
and amino acid sequence [SEQ ID NO: 2]

5'AGCTGGGAAGGGTTAAAGGCCCCCGGCTCCCTGCCCCCTGCCCTGGGGAACCCCT

```
                      (1)
GGCCCTGCGGGGAC ATG AAC TGT GTT TGC CGC CTG GTC CTG GTC
               M   N   C   V   C   R   L   V   L   V

GTG CTG AGC CTG TGG CCA GAT ACA GCT GTC GCC CCT GGG CCA
 V   L   S   L   W   P   D   T   A   V   A   P   G   P

CCA CCT GGC CCC CCT CGA GTT TCC CCA GAC CCT CGG GCC GAG
 P   P   G   P   P   R   V   S   P   D   P   R   A   E

CTG GAC AGC ACC GTG CTC CTG ACC CGC TCT CTC CTG GCG GAC
 L   D   S   T   V   L   L   T   R   S   L   L   A   D

ACG CGG CAG CTG GCT GCA CAG CTG AGG GAC AAA TTC CCA GCT
 T   R   Q   L   A   A   Q   L   R   D   K   F   P   A

GAC GGG GAC CAC AAC CTG GAT TCC CTG CCC ACC CTG GCC ATG
 D   G   D   H   N   L   D   S   L   P   T   L   A   M

AGT GCG GGG GCA CTG GGA GCT CTA CAG CTC CCA GGT GTG CTG
 S   A   G   A   L   G   A   L   Q   L   P   G   V   L

ACA AGG CTG CGA GCG GAC CTA CTG TCC TAC CTG CGG CAC GTG
 T   R   L   R   A   D   L   L   S   Y   L   R   H   V

CAG TGG CTG CGC CGG GCA GGT GGC TCT TCC CTG AAG ACC CTG
 Q   W   L   R   R   A   G   G   S   S   L   K   T   L

GAG CCC GAG CTG GGC ACC CTG CAG GCC CGA CTG GAC CGG CTG
 E   P   E   L   G   T   L   Q   A   R   L   D   R   L

CTG CGC CGG CTG CAG CTC CTG ATG TCC CGC CTG GCC CTG CCC
 L   R   R   L   Q   L   L   M   S   R   L   A   L   P

CAG CCA CCC CCG GAC CCG CCG GCG CCC CCG CTG GCG CCC CCC
 Q   P   P   P   D   P   P   A   P   P   L   A   P   P
```

FIGURE 1A

| TCC | TCA | GCC | TGG | GGG | GGC | ATC | AGG | GCC | GCC | CAC | GCC | ATC | CTG |
| S | S | A | W | G | G | I | R | A | A | H | A | I | L |

| GGG | GGG | CTG | CAC | CTG | ACA | CTT | GAC | TGG | GCC | GTG | AGG | GGA | CTG |
| G | G | L | H | L | T | L | D | W | A | V | R | G | L |

(199)

| CTG | CTG | CTG | AAG | ACT | CGG | CTG | TGA | CCCGAGGCCCAGAGCCACCACCGT |
| L | L | L | K | T | R | L | | |

CCTTCCAAAGCCACATCTTATTTATTTATTTATTTCGGTACTGGGGGCGAAACAGC

CAGGTGATCCCCCTGCCTTTAGCTCCCCCTAGTTAGAGACAGTCCTTCCGTGAGGC

TGGGGGGCATCTGTGCCTTATTTATACTTATTTATTTCAGGAGCGGGGGTGGGCTC

CTGGGTCCCCGAGGAGGAGGGAGCTGGGGTCCCGGATTCTTGTGTCCACAGACTTC

TGCCCTGGCTCCTCCCCCTCGAGGCCTGGGCAGGAATACATACTATTTATTTAAGA

GCTC

FIGURE 2 pALtrxA/EK/IL-11ΔPro-581
SEQ ID NO:3 and SEQ ID NO:4

| | | | | |
|---|---|---|---|---|
| GACGAAAGGG | CCTCGTGATA | CGCCTATTTT | TATAGGTTAA | 40 |
| TGTCATGATA | ATAATGGTTT | CTTAGACGTC | AGGTGGCACT | 80 |
| TTTCGGGGAA | ATGTGCGCGG | AACCCCTATT | TGTTTATTTT | 120 |
| TCTAAATACA | TTCAAATATG | TATCCGCTCA | TGAGACAATA | 160 |
| ACCCTGATAA | ATGCTTCAAT | AATATTGAAA | AAGGAAGAGT | 200 |
| ATGAGTATTC | AACATTTCCG | TGTCGCCCTT | ATTCCCTTTT | 240 |
| TTGCGGCATT | TTGCCTTCCT | GTTTTTGCTC | ACCCAGAAAC | 280 |
| GCTGGTGAAA | GTAAAAGATG | CTGAAGATCA | GTTGGGTGCA | 320 |
| CGAGTGGGTT | ACATCGAACT | GGATCTCAAC | AGCGGTAAGA | 360 |
| TCCTTGAGAG | TTTTCGCCCC | GAAGAACGTT | TTCCAATGAT | 400 |
| GAGCACTTTT | AAAGTTCTGC | TATGTGGCGC | GGTATTATCC | 440 |
| CGTATTGACG | CCGGGCAAGA | GCAACTCGGT | CGCCGCATAC | 480 |
| ACTATTCTCA | GAATGACTTG | GTTGAGTACT | CACCAGTCAC | 520 |
| AGAAAAGCAT | CTTACGGATG | GCATGACAGT | AAGAGAATTA | 560 |
| TGCAGTGCTG | CCATAACCAT | GAGTGATAAC | ACTGCGGCCA | 600 |
| ACTTACTTCT | GACAACGATC | GGAGGACCGA | AGGAGCTAAC | 640 |
| CGCTTTTTTG | CACAACATGG | GGATCATGT | AACTCGCCTT | 680 |
| GATCGTTGGG | AACCGGAGCT | GAATGAAGCC | ATACCAAACG | 720 |
| ACGAGCGTGA | CACCACGATG | CCTGTAGCAA | TGGCAACAAC | 760 |
| GTTGCGCAAA | CTATTAACTG | GCGAACTACT | TACTCTAGCT | 800 |
| TCCCGGCAAC | AATTAATAGA | CTGGATGGAG | GCGGATAAAG | 840 |
| TTGCAGGACC | ACTTCTGCGC | TCGGCCCTTC | CGGCTGGCTG | 880 |
| GTTTATTGCT | GATAAATCTG | GAGCCGGTGA | GCGTGGGTCT | 920 |
| CGCGGTATCA | TTGCAGCACT | GGGGCCAGAT | GGTAAGCCCT | 960 |
| CCCGTATCGT | AGTTATCTAC | ACGACGGGGA | GTCAGGCAAC | 1000 |

FIGURE 2A

| | | | | |
|---|---|---|---|---|
| TATGGATGAA | CGAAATAGAC | AGATCGCTGA | GATAGGTGCC | 1040 |
| TCACTGATTA | AGCATTGGTA | ACTGTCAGAC | CAAGTTTACT | 1080 |
| CATATATACT | TTAGATTGAT | TTAAACTTC | ATTTTTAATT | 1120 |
| TAAAAGGATC | TAGGTGAAGA | TCCTTTTTGA | TAATCTCATG | 1160 |
| ACCAAAATCC | CTTAACGTGA | GTTTTCGTTC | CACTGAGCGT | 1200 |
| CAGACCCCGT | AGAAAAGATC | AAAGGATCTT | CTTGAGATCC | 1240 |
| TTTTTTTCTG | CGCGTAATCT | GCTGCTTGCA | AACAAAAAAA | 1280 |
| CCACCGCTAC | CAGCGGTGGT | TTGTTTGCCG | GATCAAGAGC | 1320 |
| TACCAACTCT | TTTTCCGAAG | GTAACTGGCT | TCAGCAGAGC | 1360 |
| GCAGATACCA | AATACTGTCC | TTCTAGTGTA | GCCGTAGTTA | 1400 |
| GGCCACCACT | TCAAGAACTC | TGTAGCACCG | CCTACATACC | 1440 |
| TCGCTCTGCT | AATCCTGTTA | CCAGTGGCTG | CTGCCAGTGG | 1480 |
| CGATAAGTCG | TGTCTTACCG | GGTTGGACTC | AAGACGATAG | 1520 |
| TTACCGGATA | AGGCGCAGCG | GTCGGGCTGA | ACGGGGGGTT | 1560 |
| CGTGCACACA | GCCCAGCTTG | GAGCGAACGA | CCTACACCGA | 1600 |
| ACTGAGATAC | CTACAGCGTG | AGCATTGAGA | AAGCGCCACG | 1640 |
| CTTCCCGAAG | GGAGAAAGGC | GGACAGGTAT | CCGGTAAGCG | 1680 |
| GCAGGGTCGG | AACAGGAGAG | CGCACGAGGG | AGCTTCCAGG | 1720 |
| GGGAAACGCC | TGGTATCTTT | ATAGTCCTGT | CGGGTTTCGC | 1760 |
| CACCTCTGAC | TTGAGCGTCG | ATTTTTGTGA | TGCTCGTCAG | 1800 |
| GGGGGCGGAG | CCTATGGAAA | AACGCCAGCA | ACGCGGCCTT | 1840 |
| TTTACGGTTC | CTGGCCTTTT | GCTGGCCTTT | TGCTCACATG | 1880 |
| TTCTTTCCTG | CGTTATCCCC | TGATTCTGTG | GATAACCGTA | 1920 |
| TTACCGCCTT | TGAGTGAGCT | GATACCGCTC | GCCGCAGCCG | 1960 |
| AACGACCGAG | CGCAGCGAGT | CAGTGAGCGA | GGAAGCGGAA | 2000 |
| GAGCGCCCAA | TACGCAAACC | GCCTCTCCCC | GCGCGTTGGC | 2040 |
| CGATTCATTA | ATGCAGAATT | GATCTCTCAC | CTACCAAACA | 2080 |

FIGURE 2B

```
ATGCCCCCCT GCAAAAAATA AATTCATATA AAAAACATAC         2120

AGATAACCAT CTGCGGTGAT AAATTATCTC TGGCGGTGTT         2160

GACATAAATA CCACTGGCGG TGATACTGAG CACATCAGCA         2200

GGACGCACTG ACCACCATGA ATTCAAGAAG GAGATATACA         2240
```

```
T ATG AGC GAT AAA ATT ATT CAC CTG ACT GAC GAC       2274
  Met Ser Asp Lys Ile Ile His Leu Thr Asp Asp
   1           5                       10

AGT TTT GAC ACG GAT GTA CTC AAA GCG GAC GGG         2307
Ser Phe Asp Thr Asp Val Leu Lys Ala Asp Gly
             15                  20

GCG ATC CTC GTC GAT TTC TGG GCA GAG TGG TGC         2340
Ala Ile Leu Val Asp Phe Trp Ala Glu Trp Cys
             25                  30

GGT CCG TGC AAA ATG ATC GCC CCG ATT CTG GAT         2373
Gly Pro Cys Lys Met Ile Ala Pro Ile Leu Asp
         35              40

GAA ATC GCT GAC GAA TAT CAG GGC AAA CTG ACC         2406
Glu Ile Ala Asp Glu Tyr Gln Gly Lys Leu Thr
 45                  50                  55

GTT GCA AAA CTG AAC ATC GAT CAA AAC CCT GGC         2439
Val Ala Lys Leu Asn Ile Asp Gln Asn Pro Gly
                 60                  65

ACT GCG CCG AAA TAT GGC ATC CGT GGT ATC CCG         2472
Thr Ala Pro Lys Tyr Gly Ile Arg Gly Ile Pro
             70                  75

ACT CTG CTG CTG TTC AAA AAC GGT GAA GTG GCG         2505
Thr Leu Leu Leu Phe Lys Asn Gly Glu Val Ala
             80                  85

GCA ACC AAA GTG GGT GCA CTG TCT AAA GGT CAG         2538
Ala Thr Lys Val Gly Ala Leu Ser Lys Gly Gln
     90                  95

TTG AAA GAG TTC CTC GAC GCT AAC CTG GCC GGT         2571
Leu Lys Glu Phe Leu Asp Ala Asn Leu Ala Gly
100              105                 110

TCT GGT TCT GGT GAT GAC GAT GAC AAA GGT CCA         2604
Ser Gly Ser Gly Asp Asp Asp Asp Lys Gly Pro
                115                 120
```

FIGURE 2C

| | | | | | | | | | | |
|---|---|---|---|---|---|---|---|---|---|---|
| CCA | CCA | GGT | CCA | CCT | CGA | GTT | TCC | CCA | GAC | CCT | 2637 |
| Pro | Pro | Gly | Pro | Pro | Arg | Val | Ser | Pro | Asp | Pro | |
| | | | 125 | | | | | 130 | | | |
| CGG | GCC | GAG | CTG | GAC | AGC | ACC | GTG | CTC | CTG | ACC | 2670 |
| Arg | Ala | Glu | Leu | Asp | Ser | Thr | Val | Leu | Leu | Thr | |
| | | 135 | | | | | 140 | | | | |
| CGC | TCT | CTC | CTG | GCG | GAC | ACG | CGG | CAG | CTG | GCT | 2703 |
| Arg | Ser | Leu | Leu | Ala | Asp | Thr | Arg | Gln | Leu | Ala | |
| | 145 | | | | | 150 | | | | | |
| GCA | CAG | CTG | AGG | GAC | AAA | TTC | CCA | GCT | GAC | GGG | 2736 |
| Ala | Gln | Leu | Arg | Asp | Lys | Phe | Pro | Ala | Asp | Gly | |
| 155 | | | | | 160 | | | | | 165 | |
| GAC | CAC | AAC | CTG | GAT | TCC | CTG | CCC | ACC | CTG | GCC | 2769 |
| Asp | His | Asn | Leu | Asp | Ser | Leu | Pro | Thr | Leu | Ala | |
| | | | | 170 | | | | | 175 | | |
| ATG | AGT | GCG | GGG | GCA | CTG | GGA | GCT | CTA | CAG | CTC | 2802 |
| Met | Ser | Ala | Gly | Ala | Leu | Gly | Ala | Leu | Gln | Leu | |
| | | | 180 | | | | | 185 | | | |
| CCA | GGT | GTG | CTG | ACA | AGG | CTG | CGA | GCG | GAC | CTA | 2835 |
| Pro | Gly | Val | Leu | Thr | Arg | Leu | Arg | Ala | Asp | Leu | |
| | | 190 | | | | | 195 | | | | |
| CTG | TCC | TAC | CTG | CGG | CAC | GTG | CAG | TGG | CTG | CGC | 2868 |
| Leu | Ser | Tyr | Leu | Arg | His | Val | Gln | Trp | Leu | Arg | |
| | 200 | | | | | 205 | | | | | |
| CGG | GCA | GGT | GGC | TCT | TCC | CTG | AAG | ACC | CTG | GAG | 2901 |
| Arg | Ala | Gly | Gly | Ser | Ser | Leu | Lys | Thr | Leu | Glu | |
| 210 | | | | | 215 | | | | | 220 | |
| CCC | GAG | CTG | GGC | ACC | CTG | CAG | GCC | CGA | CTG | GAC | 2934 |
| Pro | Glu | Leu | Gly | Thr | Leu | Gln | Ala | Arg | Leu | Asp | |
| | | | | 225 | | | | | 230 | | |
| CGG | CTG | CTG | CGC | CGG | CTG | CAG | CTC | CTG | ATG | TCC | 2967 |
| Arg | Leu | Leu | Arg | Arg | Leu | Gln | Leu | Leu | Met | Ser | |
| | | | 235 | | | | | 240 | | | |
| CGC | CTG | GCC | CTG | CCC | CAG | CCA | CCC | CCG | GAC | CCG | 3000 |
| Arg | Leu | Ala | Leu | Pro | Gln | Pro | Pro | Pro | Asp | Pro | |
| | | 245 | | | | | 250 | | | | |
| CCG | GCG | CCC | CCG | CTG | GCG | CCC | CCC | TCC | TCA | GCC | 3033 |
| Pro | Ala | Pro | Pro | Leu | Ala | Pro | Pro | Ser | Ser | Ala | |
| | 255 | | | | | 260 | | | | | |

FIGURE 2D

| | | | | | | | | | | |
|---|---|---|---|---|---|---|---|---|---|---|
| TGG | GGG | GGC | ATC | AGG | GCC | GCC | CAC | GCC | ATC | CTG |
| Trp | Gly | Gly | Ile | Arg | Ala | Ala | His | Ala | Ile | Leu |
| 265 | | | | 270 | | | | | | 275 |

3066

| | | | | | | | | | | |
|---|---|---|---|---|---|---|---|---|---|---|
| GGG | GGG | CTG | CAC | CTG | ACA | CTT | GAC | TGG | GCC | GTG |
| Gly | GLy | Leu | His | Leu | Thr | Leu | Asp | Trp | Ala | Val |
| | | | | 280 | | | | | 285 | |

3099

| | | | | | | | | | | |
|---|---|---|---|---|---|---|---|---|---|---|
| AGG | GGA | CTG | CTG | CTG | CTG | AAG | ACT | CGG | CTG | TGA |
| Arg | Gly | Leu | Leu | Leu | Leu | Lys | Thr | Arg | Leu | |
| | | | 290 | | | | | 295 | | |

3132

AAGCTTATCG ATACCGTCGA CCTGCAGTAA TCGTACAGGG     3172

TAGTACAAAT AAAAAAGGCA CGTCAGATGA CGTGCCTTTT     3212

TTCTTGTGAG CAGTAAGCTT GGCACTGGCC GTCGTTTTAC     3252

AACGTCGTGA CTGGGAAAAC CCTGGCGTTA CCCAACTTAA     3292

TCGCCTTGCA GCACATCCCC CTTTCGCCAG CTGGCGTAAT     3332

AGCGAAGAGG CCCGCACCGA TCGCCCTTCC CAACAGTTGC     3372

GCAGCCTGAA TGGCGAATGG CGCCTGATGC GGTATTTTCT     3412

CCTTACGCAT CTGTGCGGTA TTTCACACCG CATATATGGT     3452

GCACTCTCAG TACAATCTGC TCTGATGCCG CATAGTTAAG     3492

CCAGCCCCGA CACCCGCCAA CACCCGCTGA CGCGCCCTGA     3532

CGGGCTTGTC TGCTCCCGGC ATCCGCTTAC AGACAAGCTG     3572

TGACCGTCTC CGGGAGCTGC ATGTGTCAGA GGTTTTCACC     3612

GTCATCACCG AAACGCGCGA     3632

METHOD FOR MAINTAINING GUT EPITHELIAL CELLS BY TREATMENT WITH A CYTOKINE SUCH AS INTERLEUKIN 11

This work was supported by grants by the National Institutes of Health Grant Nos. 1 PO1 HL45168- 01A1 and 1R01 HL46528-01. The government has certain rights in this invention.

FIELD OF THE INVENTION

This invention provides a method of treating patients having disorders characterized by cell damage or destruction, and more specifically, a method of using a cytokine to regenerate populations of certain cells, particularly gut cells.

BACKGROUND OF THE INVENTION

Certain mammalian cells in their normal state are characterized by rapid division and proliferation in the body, e.g., small intestinal epithelial cells, sperm cells, hair and skin cells, and hepatocyte or liver cells. Damage to these cells can result due to certain diseases, infections, exposure to therapeutic agents and treatments, exposure to other chemical or biological agents and injury or trauma.

For example, the use of chemotherapy and radiation therapy for the treatment of cancer and for the preparation of patients for bone marrow transplantation is toxic to the small intestinal (gut) epithelial cells. In fact, the small intestine is one of the organs most damaged by this therapy. Similarly damaged by such therapy are skin cells, hair cells and sperm cells. This cell damage, particularly to the gut cells, is the cause of significant mortality and morbidity in cancer patients undergoing therapy. Previously, such toxicity has been avoided by limiting the amount of chemotherapy or radiation administered to the patient. For example, gut cell toxicity has been diminished with radiation therapy by both decreasing the amount of radiation and giving the total dose subdivided into fractions (called 'fractionation' therapy). However, the reduced amount of therapy also has an adverse effect on the spread and growth of the cancer against which it is directed.

Certain autoimmune diseases of the gut, such as Crohn's disease and ulcerative colitis, also have been known to damage the small intestinal cells lining the gut, causing major morbidity and mortality in patients so afflicted. Treatment of autoimmune diseases of the gut include chemotherapy and immune suppression, both of which have serious side effects, among them additional damage to the rapidly dividing gut cells.

Damage to gut cells, and to other cells which grow rapidly in a normal healthy mammal can also be the result of trauma or injury to the area, or shock. Exposure to certain industrial and household chemicals, among other agents, can also severely damage normal healthy populations of these cells.

There is a need in the art for methods for treating cell damage, particularly gut cell damage caused by disease or adverse effects of chemotherapeutic and radiation treatment, exposure to other damaging agents or trauma in mammals, particularly humans.

SUMMARY OF THE INVENTION

In one aspect, this invention provides a method for treating patients having damaged or depleted cell populations selected from the group consisting of small intestinal epithelial cells, epithelial cells lining the large intestines and stomach, skin cells, hair cells, sperm cells and liver epithelial cells (hepatocytes). This method includes administering to the patient an effective amount of a selected hematopoietic growth factor or cytokine.

In another aspect, the invention provides a method of treating a patient undergoing chemotherapy or radiation therapy which involves administering a selected cytokine simultaneously with, or subsequently to, the initiation of chemotherapy or radiation treatment. The treatment with the cytokine is continued until a healthy cell population selected from the group consisting of small intestinal epithelial cells, epithelial cells lining the large intestines and stomach, skin cells, hair cells, sperm cells, and hepatocytes is restored.

In another aspect, the invention provides a method of restoring healthy cell populations selected from the group consisting of small intestinal epithelial cells, epithelial cells lining the large intestines and stomach, skin cells, hair cells, sperm cells and liver epithelial cells in patients suffering from autoimmune conditions by administering to such patients effective amounts of a selected cytokine, particularly IL-11. It is anticipated that these cytokine treatments may be made in combination with currently known and used immunosuppressive therapies.

One or more cytokines alone or in combination useful in these methods may be selected from among interleukin-11, interleukin-6, leukemia inhibitory factor (LIF), Oncostatin M, ciliary neurotrophic factor (CNTF) and interleukin-12 (also known as natural killer cell stimulatory factor). Additional cytokines which may be useful in this method include Interleukin-1, Interleukin- 3, G-CSF, GM-CSF and steel factor.

Other aspects and advantages of the present invention are described further in the following detailed description of the preferred embodiments thereof.

BRIEF DESCRIPTION OF THE DRAWINGS

FIG. 1 provides the nucleic acid sequence [SEQ ID NO:1] and predicted amino acid sequences (single letter code) [SEQ ID NO:2] of human interleukin 11.

FIG. 2 illustrates the DNA sequence of the expression plasmid pALtrxA/EK/IL-11ΔPro-581 (SEQ ID NO:3) and the amino acid sequence for the fusion protein therein (SEQ ID NO:4), described in Example 2.

DETAILED DESCRIPTION OF THE INVENTION

The invention provides a method of using a selected cytokine for the treatment of damaged or depleted cell populations, particularly those that are normally rapidly dividing populations. These include, but are not limited to, small intestinal epithelial cells, epithelial cells lining the large intestines and stomach, liver epithelial cells (hepatocytes), skin cells, hair cells, and sperm cells.

These cell populations, particularly small intestinal epithelial cells, are normally rapidly dividing cells, which are sensitive to various types of damage or depletion caused by disease, therapeutic treatment, trauma, infection, and the like. For example, gut cell populations primarily, but also skin, hair and sperm cell populations, are damaged by conventional cancer therapies. Gut cell populations are also damaged or depleted by autoimmune diseases. Skin and hair cell populations may also be damaged by autoimmune diseases, burns and alopecia. Sperm cell populations are damaged by oligospermia. Hepatocytes are also damaged by radiation, chemotherapy and physical trauma.

The methods of the present invention, which involve the administration of one or more selected cytokines, are thus useful in restoring populations of these cells regardless of the source or cause of the damage to, or depletion of, the cell population.

Cytokines are regulatory proteins that deliver signals between cells of the immune system, and have regulatory effects on cells of the hematopoietic and immune systems. One preferred cytokine for use in treating damaged cell populations is IL-11, a mammalian cytokine, which has been known to be useful in the treatment of selected diseases of the bone marrow and for directly or indirectly stimulating the production or function of B cells. IL-11 is described in detail in International Application, PCT/US90/06803, published May, 30, 1991, and incorporated by reference herein.

The cloned human IL-11 sequence illustrated in FIG. 1 [SEQ ID NO:1 and 2], was deposited with the ATCC, 12301 Parklawn Drive, Rockville, Md. on Mar. 30, 1990 under ATCC No. 68284. Further, as described in the examples below, IL-11 may also be produced recombinantly as a fusion protein with another protein. FIG. 2 [SEQ ID NO:3 and 4] provides such a fusion sequence with *E. coli* thioredoxin. These sequences enable the production of IL-11 in a variety of host cells by resort to now conventional genetic engineering techniques.

IL-11 may also be obtained from certain cell lines. Human cell lines have been identified as sources of at least one species of IL-11, i.e., the human lung fibroblast cell line, MRC-5 (ATCC Accession Number CCL 171), and the human trophoblastic cell line, TPA30-1, (ATCC Accession Number CRL 1583). Other human sources for IL-11 may also be available. Additional information regarding the production of recombinant IL-11 and the isolation of IL-11 obtained from cell sources is provided in the above referenced International Application, PCT/US90/06803.

Not only is IL-11 useful in the methods of treating and restoring the cell populations above-described, but also, other cytokines are considered to be useful in the same methods. Certain cytokines which are characterized by having common signal transduction pathways with those of IL-11 are anticipated to be useful in the treatment of patients having cell damage to the selected cell populations in the same manner as is IL-11, and/or in combination with IL-11. See, N.Y. Ip et al., *Cell,* 69:1121–1132 (1992).

One such cytokine which shares common biological activities with IL-11 is Interleukin-6 (IL-6), which is described in detail in PCT patent application WO88/00206, published Jan. 14, 1988 and incorporated by reference herein. Another cytokine having this pathway is known as Natural Killer Cell Stimulatory Factor (NKSF), also termed Interleukin-12 (IL-12). This cytokine is described in detail in PCT patent application WO9205256, published Apr. 2, 1992 and incorporated by reference herein.

Still another cytokine sharing the IL-11 signal transduction pathway is Leukemia Inhibitory Factor (LIF), also known as Cholinergic Differentiation Factor (CDF), and is described in detail in PCT patent application WO90/02183, published Mar. 8, 1990, and incorporated by reference herein. Another cytokine characterized in this way is Oncostatin M (OSM), described in detail in European patent application No. 290,949, published Nov. 12, 1988 and incorporated by reference herein. Additionally, Ciliary Neurotrophic Factor (CNTF) shares this signal transduction pathway, and is anticipated to be useful in the methods of restoring these cell populations. CNTF is described in detail in PCT patent application WO9104316, published Apr. 4, 1991, and incorporated by reference herein.

It is further anticipated that other cytokines are likely to be useful in the methods of this invention, either in place of, or in combination with, IL-11 and/or one or more of the above disclosed cytokines. One additional cytokine useful in a therapeutic method or combination pharmaceutical preparation according to this invention is Interleukin-1 (IL-1). IL-1 is described in detail in European patent application No. 456,332, published Nov. 13, 1991, and incorporated by reference herein. Other cytokines which may be useful in these methods of restoring the cell populations selected from small intestinal epithelial cells, epithelial cells lining the large intestines and stomach, skin cells, hair cells, and sperm cells include Granulocyte Colony Stimulating Factor (G-CSF), Interleukin-3 (IL-3), Granulocyte-Macrophage Colony Stimulating Factor (GM-CSF) and Steel Factor (SCF). G-CSF is described in detail in PCT patent application WO9114776, published Oct. 3, 1991, and incorporated by reference herein. GM-CSF is described in detail in PCT patent application WO8600639, published Jan. 30, 1986, [see, also, European Patent Application No. 281,069, published Sep. 7, 1988] and incorporated by reference herein. IL-3 is described in detail in U.S. Pat. No. 4,959,455, issued Sep. 25, 1990, and incorporated by reference herein. SCF is described in detail in PCT patent application WO9105795, published May 2, 1991, and incorporated by reference herein.

For additional general information on these cytokines, see also, F. Takatsuki et al., *Cancer Res.,* 500:2885–2890 (1990); D. P. Gearing et al., *Science,* 255:1434–1437 (1992); G. Damia et al., *Cancer Res.,* 52:4082–4089 (1992).

For use in the methods of treatment disclosed in this invention, the above-described cytokines or biologically active fragments thereof may be prepared by genetic engineering techniques, as disclosed in the above-incorporated references. Moreover, in addition to recombinant techniques, the cytokine polypeptides described above may also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof which duplicate or partially duplicate the functionality thereof may also be used in the method of this invention. Thus, they may be employed as biologically active or immunological substitutes for the natural, purified cytokines useful in the present invention.

Modifications in the protein, peptide or DNA sequences of these cytokines or active fragments thereof may also produce proteins which may be employed in the methods of this invention. Such modified cytokines can be made by one skilled in the art using known techniques. Modifications of interest in the cytokine sequences, e.g., the IL-11 sequence, may include the replacement, insertion or deletion of one or more selected amino acid residues in the coding sequences. Mutagenic techniques for such replacement, insertion or deletion are well known to one skilled in the art. [See, e.g., U.S. Pat. No. 4,518,584.]

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present method, may also be easily made by one of skill in the art. One such modification may be the attachment of polyethylene glycol (PEG) onto existing lysine residues in the cytokine sequence or the insertion of one or more lysine residues or other amino acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions [Sambrook et al, Molecular Cloning. A Laboratory Manual., 2d edit., Cold Spring Harbor Laboratory, New York (1989)] will be similarly useful in this invention.

Also considered useful in these methods are fusion molecules, prepared by fusing the sequence or a biologically active fragment of the sequence of one cytokine to another cytokine or proteinaceous therapeutic agent, e.g., IL-11 fused to IL-6 [see, e.g., methods for fusion described in PCT Patent Application No. WO92/04455, published Mar. 19, 1992, incorporated herein by reference]. Alternatively, combinations of the cytokines may be administered together according to the method.

Thus, where in the description of the methods of this invention, a particular cytokine is mentioned by name, it is understood by those of skill in the art to encompass the protein produced by the sequences presently disclosed in the art, e.g., for IL-11, the sequences of FIG. 1 and FIG. 2, as well as proteins characterized by the modifications described above, yet which retain substantially similar activity in restoring the cell populations of one or more of the cell populations identified herein.

The present invention thus involves treating patients having damaged or depleted cell populations selected from small intestinal epithelial cells, epithelial cells lining the large intestines and stomach, liver epithelial cells, skin cells, hair cells, and sperm cells. The treatment involves administering an effective amount of a selected cytokine in a pharmaceutical carrier. This treatment enables the restoration or regeneration of the damaged or depleted cell population primarily by the stimulation, direct or indirect, of any undamaged stem cells. The stem cells are stimulated to differentiate into the cell population which had been damaged or depleted.

This invention is exemplified below in the treatment of small intestinal epithelial cells (gut cells) damaged by chemotherapy or radiation therapy with IL-11 as the selected cytokine. The effect of IL-11 on gut epithelial cells has been demonstrated by experiments, such as those illustrated in Example 2 below. For example, in studies with mice, IL-11 had a positive effect on mouse survival after exposure to 5-fluorouracil and irradiation without an effect on peripheral neutrophil (white blood cell) counts.

Where damage to, or depletion of, gut cells or other cell populations is caused by therapy, the treatment of the present invention may occur simultaneously with, or sequentially after, the therapy, e.g., chemotherapy or radiation. For example, effective amounts of IL-11 alone, another cytokine alone, or a combination of cytokines, may be administered in a suitable pharmaceutical carrier.

Preferably, treatment begins concurrently with or shortly after the chemotherapy or radiation therapy is begun and is continued until the level of the gut cells or other cells is returned to acceptable levels. However, the selected cytokine, e.g., IL-11, or combination of cytokines, may be administered for a suitable period of time prior to the beginning of chemotherapy or radiation therapy to improve the efficacy with which the cytokine, e.g., IL-11, stimulates the stem cell which differentiates into the mature gut cell.

The invention also involves methods for treating patients afflicted with damaged or depleted cell populations selected from small intestinal epithelial cells, epithelial cells lining the large intestines and stomach, liver epithelial cells, skin cells, hair cells, and sperm cells, where the damage or depletion is caused by autoimmune disease. For example, Crohn's disease, damages and depletes the population of normally rapidly dividing gut cells. Other autoimmune diseases may similarly affect the cells of the large intestine or stomach, liver, skin and hair, and sperm cells. The present invention also involves treating such conditions by administering effective doses of a selected cytokine, e.g., IL-11, or combination of cytokines.

Similarly, infection, trauma or shock can damage or deplete normal populations of gut cells, as well as the other cells mentioned herein, thereby requiring the administration of effective amounts of one or more cytokines, particularly IL-11.

In one embodiment of the present invention, a selected cytokine, IL-11, obtained by recombinant expression or prepared synthetically and purified to homogeneity, is combined with a pharmaceutical carrier suitable for internal administration. Purification is performed using conventional techniques (see, e.g., PCT/US90/06803 and the examples below).

Suitable pharmaceutically acceptable carriers facilitate administration of the cytokine, e.g., IL-11, and are well known in the art. Exemplary carriers include sterile saline, lactose, sucrose, calcium phosphate, gelatin, dextrin, agar, pectin, peanut oil, olive oil, sesame oil, and water. Additionally, the carrier or diluent includes a time delay material, such as glyceryl monostearate or glyceryl distearate alone or with a wax. In addition, slow release polymer formulations can be used. Suitable sustain-release matrices contain the active ingredient in a mixture with one or more of the following: sodium bentonite, ethylcellulose, stearic acid, calcium stearate, adipic acid, fumeric acid, polyethylene glycol, deacetylated chitin and cellulose acetate. Suitable preservatives and/or stabilizers may be included.

Alternatively, the selected cytokine, e.g., IL-11, can be combined with other conventional agents useful in alleviating the symptoms associated with chemotherapy, such as antiemetics, anti-oxidants, and other hematopoietic growth factors.

The therapeutic method of the present invention may also include co-administration or combination of a selected cytokine with other human factors known to those of skill in the art. Exemplary cytokines or hematopoietins for such use include those cytokines specifically referenced above. Growth factors, such as B cell growth factor, B cell differentiation factor, or eosinophil differentiation factors may also prove useful in co-administration with these cytokines. Other agents for co-administration may include other pharmaceutically effective chemical agents and drugs, e.g., such as agents to control infection. The dosage recited below would be adjusted to compensate for such additional components in the therapeutic composition. Progress of the treated patient can be monitored by conventional methods.

Without wishing to be bound by theory, the inventors believe that treatment of damage to, or depletion of, the normally rapidly dividing gut epithelial cells with IL-11 or another cytokine, provides two important advantages to current methods of dealing with gut toxicity. First, the cytokine, e.g., IL-11, improves the integrity of the gut by stimulating the stem cells to restore a healthy cell population, thereby preventing entry of bacteria and fungi into the blood of the treated patient. IL-11 treatment of patients can thereby reduce the morbidity and mortality associated with chemotherapy and radiation treatment-induced gut damage. Additionally, IL-11 may allow increased amounts of chemotherapy and radiation therapy to be used in cancer treatments, a highly desirable effect, since this may improve the survival rates of patients with certain cancers which are currently fatal.

Similarly, in the treatment of autoimmune diseases of the small intestine, a cytokine, such as IL-11, is expected restore the cell population thereby improving healing and reducing morbidity and mortality without the deleterious side effects of previous therapies.

The treatment of a patient with a selected cytokine, such as IL-11, or combination of cytokines is anticipated to have the same effects on other cell populations, e.g., skin, hair, sperm cells, epithelial linings of stomach and large intestines, and liver epithelial cells, which are damaged or depleted by disease, infection, shock or trauma. The cytokine is theorized to restore healthy populations by stimulating stem cells into differentiating into mature cell populations.

In the treatment of any of these conditions resulting in damage to, or depletion of, the cell population, the cytokine, e.g., IL-11, can be administered by any suitable route, but is preferably administered systemically, i.e., parenterally. Of the parental routes, subcutaneous and intraperitoneal are preferred. With chemotherapy, intravenous administration may be desired.

A suitable treatment regimen for patients undergoing chemotherapy or radiation, or for patients who have already sustained cell damage or depletion due to trauma or disease, may be determined by the attending physician based upon such factors as the patient's age, sex, weight, and general health. Generally, a suitable dose of a cytokine, e.g., IL-11, ranges between about 1 µg and about 1000 mg or 50 to 5000 units. Another suitable dose may be in the range of between about 10 µg and about 1000 mg, and more preferably about 100 µg and about 500 mg, of cytokine, e.g., IL-11, per kg of body weight. A unit is conventionally described as the concentration of polypeptide which leads to half maximal stimulation in a suitable assay, e.g., for IL-11, the T1165 assay described in PCT/US90/06803.

These doses may be administered daily for between 1 day and 6 months, or for as long as is deemed necessary, depending on the nature of the cell damage or depletion.

When used to treat autoimmune conditions, the cytokine composition, e.g., IL-11, may be formulated to contain other agents useful in alleviating the symptoms of these conditions, including e.g., prednisone, cyclosporine, cyclophosphamide, and azathioprine, as well as other known agents.

Also, where treatment is directed to skin and hair cells, a pharmaceutical preparation may be prepared using agents which are conventional for topically administering therapeutics to the skin and hair, e.g., for systemic or local or topical administration. Suitable pharmaceutical carriers for a topical composition of the present invention may include several conventional ingredients of creams, lotions, gels or ointments. Such conventional ingredients are included in skin creams or oils for topical administration for treating a variety of diseases of the skin. Such compositions may be used as drug delivery systems to transmit the IL-11 through the skin or to facilitate the absorption of the IL-11 into the skin or onto a rash or other skin eruption. [See, e.g., U.S. Pat. No. 3,981,996; U.S. Pat. No. 4,731,241; U.S. Pat. No. 4,164,563; U.S. Pat. No. 3,924,004; U.S. Pat. No. 3,888,995; U.S. Pat. No. 3,592,930; and U.S. Pat. No. 4,753,958].

The following examples illustrate the methods of the present invention employing IL-11 as the selected cytokine, and gut cell populations damaged and depleted by chemotherapy as the model rapidly growing cell population. However, these examples do not limit the scope of the invention.

EXAMPLE 1

Human IL-11

The isolation and cloning of human IL-11 is described in detail in published PCT Application No. US90/06803 and now known to the art. The full sequence for human IL-11 was determined and is shown in FIG. 1. This protein is characterized by the sequence of FIG. 1 [SEQ ID NO:1 and 2]. These descriptions are incorporated by reference herein.

EXAMPLE 2

Thioredoxin-IL-11 Fusion Molecule

IL-11 was also prepared in a fusion molecule for use in the method of the present invention. The fusion molecule contained E. coli thioredoxin and recombinant IL-11, obtained as described in PCT Application No. US90/06803 incorporated by reference [see also Paul et al, *Proc. Natl. Acad. Sci. U.S.A.*, 87:7512– 7516 (1990) and PCT Patent publication WO91/07495, published May 30, 1991 incorporated herein by reference].

The E. coli thioredoxin (trxA) gene was cloned based on its published sequence [Lim et al, *J. Bacteriol.*, 163:311–316 (1985)] and employed to construct various related E. coli expression plasmids using standard DNA manipulation techniques, described extensively by Sambrook, Fritsch and Maniatis, *Molecular Cloning. A Laboratory Manual*, 2nd edition, Cold Spring Harbor Laboratory, Cold Spring Harbor, N.Y. (1989). (Nucleotides 2242–2568 of FIG. 2 encode the E. coli thioredoxin protein.)

An expression plasmid pALtrxA-781 was constructed containing the E. coli trxA gene without fusion to another sequence. This plasmid, which directs the accumulation of >10% of the total cell protein as thioredoxin in an E. coli host strain GI724, was further manipulated to provide for the construction of a trxA/IL-11 fusion sequence, resulting in the expression vector, pALtrxA/EK/IL-11ΔPro-581.

The entire sequence of the plasmid expression vector, pALtrxA/EK/IL-11ΔPro-581 (SEQ ID NO:3 and SEQ ID NO:4), is illustrated in FIG. 2 and contains the following principal features:

Nucleotides 1-2060 contain DNA sequences originating from the plasmid pUC-18 [Norrander et al, *Gene*, 26: 101–106 (1983)] including sequences containing the gene for β-lactamase which confers resistance to the antibiotic ampicillin in host *E. coli* strains, and a colE1-derived origin of replication. Nucleotides 2061– 2221 contain DNA sequences for the major leftward promoter (pL) of bacteriophage λ [Sanger et al, *J. Mol. Biol.*, 162:729–773 (1982)], including three operator sequences, $O_L1$, $O_L2$ and $OL_3$. The operators are the binding sites for λcI repressor protein, intracellular levels of which control the amount of transcription initiation from pL. Nucleotides 2222–2241 contain a strong ribosome binding sequence derived from that of gene 10 of bacteriophage T7 [Dunn and Studier, *J. Mol. Biol.*, 166:477–535 (1983)].

Nucleotides 2242–2568 contain a DNA sequence encoding the *E. coli* thioredoxin protein [Lim et al, *J. Bacteriol.*, 163:311–316 (1985)]. There is no translation termination codon at the end of the thioredoxin coding sequence in this plasmid.

Nucleotides 2569–2583 contain DNA sequence encoding the amino acid sequence for a short, hydrophilic, flexible spacer peptide "--GSGSG--". Nucleotides 2584–2598 provide DNA sequence encoding the amino acid sequence for the cleavage recognition site of enterokinase (EC 3.4.4.8), "--DDDDK--" [Maroux et al, *J. Biol. Chem.*, 246:5031–5039 (1971)].

Nucleotides 2599–3132 contain DNA sequence encoding the amino acid sequence of a modified form of mature human IL-11 [Paul et al, *Proc. Natl. Acad. Sci. USA*, 87:7512–7516 (1990)], the N-terminal prolyl-residue normally found in the natural protein has been deleted. Thus, these nucleotides encode IL-11 beginning with amino acid #2 of the mature native sequence. The sequence includes a translation termination codon at the 3'-end of the IL-11 sequence.

Nucleotides 3133–3159 provide a "Linker" DNA sequence containing restriction endonuclease sites. Nucleotides 3160–3232 provide a transcription termination sequence based on that of the *E. coli* aspA gene [Takagi et al, *Nucl. Acids Res.*, 13:2063–2074 (1985)]. Nucleotides 3233–3632 are DNA sequences derived from pUC- 18.

As described in Example 3 below, when cultured under the appropriate conditions in a suitable *E. coli* host strain, this plasmid vector can direct the production of high levels (approximately 10% of the total cellular protein) of a thioredoxin-IL-11 fusion protein. By contrast, when not fused to thioredoxin, IL-11 accumulated to only 0.2% of the total cellular protein when expressed in an analogous host/vector system.

EXAMPLE 3

Expression of a Fusion Protein

A thioredoxin-IL-11 fusion protein was produced according to the following protocol using the plasmid constructed as described in Example 2. pALtrxA/EK/IL-11ΔPro-581 (SEQ ID NO: 3) was transformed into the *E. coli* host strain GI724 (F−, lacI$^q$, lacP$^{L8}$, ampC::λcI$^+$) by the procedure of Dagert and Ehrlich, *Gene*, 6: 23 (1979). The untransformed host strain *E. coli* GI724 was deposited with the American Type Culture Collection, 12301 Parklawn Drive, Rockville, Md. on Jan. 31, 1991 under ATCC No. 55151 for patent purposes pursuant to applicable laws and regulations. Transformants were selected on 1.5% w/v agar plates containing IMC medium, which is composed of M9 medium [Miller, "Experiments in Molecular Genetics" Cold Spring Harbor Laboratory, New York (1972)] supplemented with 0.5% w/v glucose, 0.2% w/v casamino acids and 100 µg/ml ampicillin.

GI724 contains a copy of the wild-type λcI repressor gene stably integrated into the chromosome at the ampC locus, where it has been placed under the transcriptional control of *Salmonella typhimurium* trp promoter/operator sequences. In GI724, λcI protein is made only during growth in tryptophan-free media, such as minimal media or a minimal medium supplemented with casamino acids such as IMC, described above. Addition of tryptophan to a culture of GI724 will repress the trp promoter and turn off synthesis of λcI, gradually causing the induction of transcription from pL promoters if they are present in the cell.

GI724 transformed with pALtrxA/EK/IL-11ΔPro-581 (SEQ ID NO:3 and SEQ ID NO:4) was grown at 37° C. to an $A_{550}$ of 0.5 in IMC medium. Tryptophan was added to a final concentration of 100 µg/ml and the culture incubated for a further 4 hours. During this time thioredoxin-IL-11 fusion protein accumulated to approximately 10% of the total cell protein.

All of the fusion protein was found to be in the soluble cellular fraction, and was purified as follows. Cells were lysed in a French pressure cell at 20,000 psi in 50 mM HEPES pH 8.0, 1 mM phenylmethylsulfonyl fluoride. The lysate was clarified by centrifugation at 15,000× g for 30 minutes and the supernatant loaded onto a QAE-Toyopearl column. The flow-through fractions were discarded and the fusion protein eluted with 50 mM HEPES pH 8.0, 100 mM NaCl. The eluate was adjusted to 2M NaCl and loaded onto a column of phenyl-Toyopearl. The flow-through fractions were again discarded and the fusion protein eluted with 50 mM HEPES pH 8.0, 0.5 M NaCl.

The fusion protein was then dialyzed against 25 mM HEPES pH 8.0 and was >80% pure at this stage. By T1165 bioassay [Paul et al, cited above] the purified thioredoxin-IL-11 protein exhibited an activity of $8\times10^5$ U/mg. This value agrees closely on a molar basis with the activity of $2\times10^6$ U/mg found for COS cell-derived IL-11 in the same assay. One milligram of the fusion protein was cleaved at 37° C. for 20 hours with 1000 units of bovine enterokinase [Leipnieks and Light, *J. Biol. Chem.*, 254:1677–1683 (1979)] in 1 ml 10mM Tris-Cl (pH8.0)/10 mM CaCl$_2$. IL-11 could be recovered from the reaction products by passing them over a QAE-Toyopearl column in 25 mM HEPES pH 8.0, where IL-11 was found in the flow-through fractions. Uncleaved fusion protein, thioredoxin and enterokinase remained bound on the column.

EXAMPLE 4

Treatment of Irradiated Mice

The IL-11 used in the tests below was obtained from Genetics Institute, Inc., Cambridge, Mass. and was prepared in *E. coli* essentially as described in the examples above. The IL-11 (140 µg/ml) was then mixed with 10 mM Tris buffer, to a pH of about 8.0. The level of endotoxin in this in vivo grade formulation is about 1.4 eu/mg of protein. The preparation also contains about 10% molar hydroxylmate and about 3 ng/ml (0.002%) thioredoxin.

Eight-ten week old C3H/HeJ (Jackson Labs) mice were administered intraperitoneally (i.p.) 150 mg/kg 5-fluorouracil (5-FU) diluted in Hanks Balanced Salt Solution (HBSS) containing 0.024 M Hepes buffer [both Gibco], three days prior to sublethal irradiation. Irradiation consisted of 6.0 Gys TBI delivered by Siemens 250 Kvp X-ray therapy machine, filtered with 1.0 mm Cu, giving half value layer of 2.1 mm Cu at 50 cm SSD, and with a dose rate of 78.13 (cGy/min). On the same day as the irradiation dose was given, mice were administered the above-described recombinant in vivo grade human IL-11 (Genetics Institute) at a divided dose (twice/day) of 250 micrograms/kg/day. These divided doses were given in 0.2 ml volumes subcutaneously in HBSS with Hepes and 0.1% bovine serum albumin (BSA; Boehringer-Mannheim). Control animals received the same volume of HBSS and BSA without IL-11. Treatment was continued for 9 to 18 days post-irradiation or until animals died.

Hematologic analysis of leukocyte cell counts and platelet counts were performed on tail vein bleeds on a Coulter Model ZM (Coulter Electronics) using a 100 micron aperture for leukocyte determinations and a 50 micron aperture for platelet determinations. Red blood cells were lysed using Zapglobin (Coulter) according to manufacturer's recommendations. Blood smears were stained with Wright-Giemsa using standard methods and examined at 100× for differential analysis. The absolute numbers of neutrophils, lymphocytes, monocytes, and eosinophils in the peripheral blood was calculated by multiplying the total leukocyte counts with the percentage of leukocytes obtained on the differential. Peripheral blood hematocrits were performed by spinning capillary tubes for five minutes in a Clay-Adams hematocrit centrifuge.

Whole dead mice (dying in the course of the experiment or by sacrifice) were fixed in 10% buffered formalin overnight. One femur/mouse was fixed in Bouin's solution. Tissues from each organ (liver, spleen, kidney, small intestine mesentery, abdominal wall, lung, heart, testes, and femur) were embedded in paraffin wax using standard techniques and four micron sections were cut and stained with hematoxylin and eosin. For analysis of small intestinal crypts, ten independent measurements of villus height, crypt depth, and metaphases/crypt were made in each section of small intestine using an objective-mounted micrometer.

Results are expressed in Table I below as the mean +/– SD unless otherwise stated. The probability of significant differences when two related groups were compared was determined using a two-tailed Student t-test. The probability of significant differences when multiple treatments were examined was determined by analysis of variance followed by Student-Newman-Keuls multiple range tests to define the unique subsets within the study.

In three separate experiments, all control mice died between day 3 and day 10 after irradiation, while only 3/13 (23%) of IL-11 treated mice died (on days 4, 9, 10 post-irradiation). In experiment 1, all control animals died by day 9. Animals were autopsied on the day of death or (in the treated group) on day 9 by sacrificing remaining animals (day of examination listed in Table I. At autopsy, 4/5 mice in the control group had macroscopic infection foci in the liver compared to 2/5 of the IL-11 treated mice. In addition, the foci present in IL-11 treated mice were present in fewer numbers and smaller in size (Table I). These foci subsequently were demonstrated to contain *E. coli* bacteria by identification using microbiological analysis. Microscopically many foci (12–129/random section) were found within the liver from control mice, while fewer (6–21/section) were demonstrated in IL-11 treated mice (Table I). Similar bacterial foci were also seen in the mesentery and spleen of animals.

Surprisingly, these differences in mortality and the presence of bacterial foci in organs of mice were not associated with differences in peripheral leukocyte counts or absolute neutrophil counts as shown by data in Table II.

Since *E. coli* are a known resident organism of the small intestine, the increase in bacterial infection and mortality in the control animals probably reflects gut toxicity from irradiation and chemotherapy. Histologic section of the small intestine and morphometric quantitation of the length of the small intestine villi confirmed extensive damage in control mice as shown by data in Table III. In contrast, IL-11 treatment was associated with almost complete preservation of villi length (Table III). In addition, IL-11 treated mice demonstrated near normal numbers of mitotic crypt cells, a further indication of stimulation of proliferation of crypt progenitor or stem cells.

These data demonstrate that the administration of IL-11 in vivo has marked positive effects on the recovery of small intestinal crypt epithelial cells from the combined cytotoxic effects of radiation and chemotherapy.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for maintaining a gut epithelial cell population comprising the step of administering to a patient a pharmacologically effective amount of a cytokine selected from the group consisting of interleukin-11, interleukin-6, leukemia inhibitory factor, oncostatin M, and ciliary neurotrophic factor.

2. The method of claim 1, further comprising administering an additional cytokine.

3. A method for maintaining a gut epithelial cell population comprising the step of administering to a patient a pharmacologically effective amount of IL-11.

4. A method for maintaining a gut epithelial cell population comprising the step of administering to a patient a pharmacologically effective amount of IL-6.

5. A method for maintaining a small intestinal epithelial cell population comprising the step of administering to a patient a pharmaceutically effective amount of a cytokine selected from the group consisting of interleukin-11, interleukin-6, leukemia inhibitory factor, oncostatin M, and ciliary neurotrophic factor.

6. The method of claim 5, further comprising administering an additional cytokine.

7. A method for maintaining a small intestinal epithelial cell population comprising the step of administering to a patient a pharmaceutically effective amount of IL-11.

8. A method for maintaining a small intestinal epithelial cell population comprising the step of administering to a patient a pharmaceutically effective amount of IL-6.

9. A method for maintaining a large intestinal epithelial cell population comprising the step of administering to a patient a pharmaceutically effective amount of a cytokine selected from the group consisting of interleukin-11, interleukin-6, leukemia inhibitory factor, oncostatin M, and ciliary neurotrophic factor.

10. The method of claim 9, further comprising administering an additional cytokine.

11. A method for maintaining a large intestinal epithelial cell population comprising the step of administering to a patient a pharmaceutically effective amount of IL-11.

12. A method for maintaining a large intestinal epithelial cell population comprising the step of administering to a patient a pharmaceutically effective amount of IL-6.

* * * * *

UNITED STATES PATENT AND TRADEMARK OFFICE
CERTIFICATE OF CORRECTION

Page 1 of 15

PATENT NO. : 5,460,810
DATED : October 24, 1995
INVENTOR(S) : David A. Williams, et al.

It is certified that error appears in the above-identified patent and that said Letters Patent is hereby corrected as shown below:

On the title page, item [56]: References Cited, under OTHER PUBLICATIONS, please change

"IP et al., Cell 63:1121-1132 (1992)." to read: --IP et al., Cell 69:1121-1132 (1992).--

Delete columns 1-14, and substitute the attached columns 1-28

Signed and Sealed this

Eleventh Day of February, 1997

Attest:

BRUCE LEHMAN

*Attesting Officer*    *Commissioner of Patents and Trademarks*

METHOD FOR MAINTAINING GUT EPITHELIAL CELLS BY TREATMENT WITH A CYTOKINE SUCH AS INTERLEUKIN 11

This work was supported by grants by the National Institutes of Health Grant Nos. 1 PO1 HL45168- 01A1 and 1R01 HL46528-01. The government has certain rights in this invention.

FIELD OF THE INVENTION

This invention provides a method of treating patients having disorders characterized by cell damage or destruction, and more specifically, a method of using a cytokine to regenerate populations of certain cells, particularly gut cells.

BACKGROUND OF THE INVENTION

Certain mammalian cells in their normal state are characterized by rapid division and proliferation in the body, e.g., small intestinal epithelial cells, sperm cells, hair and skin cells, and hepatocyte or liver cells. Damage to these cells can result due to certain diseases, infections, exposure to therapeutic agents and treatments, exposure to other chemical or biological agents and injury or trauma.

For example, the use of chemotherapy and radiation therapy for the treatment of cancer and for the preparation of patients for bone marrow transplantation is toxic to the small intestinal (gut) epithelial cells. In fact, the small intestine is one of the organs most damaged by this therapy. Similarly damaged by such therapy are skin cells, hair cells and sperm cells. This cell damage, particularly to the gut cells, is the cause of significant mortality and morbidity in cancer patients undergoing therapy. Previously, such toxicity has been avoided by limiting the amount of chemotherapy or radiation administered to the patient. For example, gut cell toxicity has been diminished with radiation therapy by both decreasing the amount of radiation and giving the total dose subdivided into fractions (called 'fractionation' therapy). However, the reduced amount of therapy also has an adverse effect on the spread and growth of the cancer against which it is directed.

Certain autoimmune diseases of the gut, such as Crohn's disease and ulcerative colitis, also have been known to damage the small intestinal cells lining the gut, causing major morbidity and mortality in patients so afflicted. Treatment of autoimmune diseases of the gut include chemotherapy and immune suppression, both of which have serious side effects, among them additional damage to the rapidly dividing gut cells.

Damage to gut cells, and to other cells which grow rapidly in a normal healthy mammal can also be the result of trauma or injury to the area, or shock. Exposure to certain industrial and household chemicals, among other agents, can also severely damage normal healthy populations of these cells.

There is a need in the art for methods for treating cell damage, particularly gut cell damage caused by disease or adverse effects of chemotherapeutic and radiation treatment, exposure to other damaging agents or trauma in mammals, particularly humans.

SUMMARY OF THE INVENTION

In one aspect, this invention provides a method for treating patients having damaged or depleted cell populations selected from the group consisting of small intestinal epithelial cells, epithelial cells lining the large intestines and stomach, skin cells, hair cells, sperm cells and liver epithelial cells (hepatocytes). This method includes administering to the patient an effective amount of a selected hematopoietic growth factor or cytokine.

In another aspect, the invention provides a method of treating a patient undergoing chemotherapy or radiation therapy which involves administering a selected cytokine simultaneously with, or subsequently to, the initiation of chemotherapy or radiation treatment. The treatment with the cytokine is continued until a healthy cell population selected from the group consisting of small intestinal epithelial cells, epithelial cells lining the large intestines and stomach, skin cells, hair cells, sperm cells, and hepatocytes is restored.

In another aspect, the invention provides a method of restoring healthy cell populations selected from the group consisting of small intestinal epithelial cells, epithelial cells lining the large intestines and stomach, skin cells, hair cells, sperm cells and liver epithelial cells in patients suffering from autoimmune conditions by administering to such patients effective amounts of a selected cytokine, particularly IL-11. It is anticipated that these cytokine treatments may be made in combination with currently known and used immunosuppressive therapies.

One or more cytokines alone or in combination useful in these methods may be selected from among interleukin-11, interleukin-6, leukemia inhibitory factor (LIF), Oncostatin M, ciliary neurotrophic factor (CNTF) and interleukin-12 (also known as natural killer cell stimulatory factor). Additional cytokines which may be useful in this method include Interleukin-1, Interleukin- 3, G-CSF, GM-CSF and steel factor.

Other aspects and advantages of the present invention are described further in the following detailed description of the preferred embodiments thereof.

BRIEF DESCRIPTION OF THE DRAWINGS

FIG. 1 provides the nucleic acid sequence [SEQ ID NO:1] and predicted amino acid sequences (single letter code) [SEQ ID NO:2] of human interleukin 11.

FIG. 2 illustrates the DNA sequence of the expression plasmid pALtrxA/EK/IL-11ΔPro-581 (SEQ ID NO:3) and the amino acid sequence for the fusion protein therein (SEQ ID NO:4), described in Example 2.

DETAILED DESCRIPTION OF THE INVENTION

The invention provides a method of using a selected cytokine for the treatment of damaged or depleted cell populations, particularly those that are normally rapidly dividing populations. These include, but are not limited to, small intestinal epithelial cells, epithelial cells lining the large intestines and stomach, liver epithelial cells (hepatocytes), skin cells, hair cells, and sperm cells.

These cell populations, particularly small intestinal epithelial cells, are normally rapidly dividing cells, which are sensitive to various types of damage or depletion caused by disease, therapeutic treatment, trauma, infection, and the like. For example, gut cell populations primarily, but also skin, hair and sperm cell populations, are damaged by conventional cancer therapies. Gut cell populations are also damaged or depleted by autoimmune diseases. Skin and hair cell populations may also be damaged by autoimmune diseases, burns and alopecia. Sperm cell populations are damaged by oligospermia. Hepatocytes are also damaged by radiation, chemotherapy and physical trauma.

The methods of the present invention, which involve the administration of one or more selected cytokines, are thus useful in restoring populations of these cells regardless of the source or cause of the damage to, or depletion of, the cell population.

Cytokines are regulatory proteins that deliver signals between cells of the immune system, and have regulatory effects on cells of the hematopoietic and immune systems. One preferred cytokine for use in treating damaged cell populations is IL-11, a mammalian cytokine, which has been known to be useful in the treatment of selected diseases of the bone marrow and for directly or indirectly stimulating the production or function of B cells. IL-11 is described in detail in International Application, PCT/US90/06803, published May, 30, 1991, and incorporated by reference herein.

The cloned human IL-11 sequence illustrated in FIG. 1 [SEQ ID NO:1 and 2], was deposited with the ATCC, 12301 Parklawn Drive, Rockville, Md. on Mar. 30, 1990 under ATCC No. 68284. Further, as described in the examples below, IL-11 may also be produced recombinantly as a fusion protein with another protein. FIG. 2 [SEQ ID NO:3 and 4] provides such a fusion sequence with *E. coli* thioredoxin. These sequences enable the production of IL-11 in a variety of host cells by resort to now conventional genetic engineering techniques.

IL-11 may also be obtained from certain cell lines. Human cell lines have been identified as sources of at least one species of IL-11, i.e., the human lung fibroblast cell line, MRC-5 (ATCC Accession Number CCL 171), and the human trophoblastic cell line, TPA30-1, (ATCC Accession Number CRL 1583). Other human sources for IL-11 may also be available. Additional information regarding the production of recombinant IL-11 and the isolation of IL-11 obtained from cell sources is provided in the above referenced International Application, PCT/US90/06803.

Not only is IL-11 useful in the methods of treating and restoring the cell populations above-described, but also, other cytokines are considered to be useful in the same methods. Certain cytokines which are characterized by having common signal transduction pathways with those of IL-11 are anticipated to be useful in the treatment of patients having cell damage to the selected cell populations in the same manner as is IL-11, and/or in combination with IL-11. See, N.Y. Ip et al., *Cell*, 69:1121–1132 (1992).

One such cytokine which shares common biological activities with IL-11 is Interleukin-6 (IL-6), which is described in detail in PCT patent application WO88/00206, published Jan. 14, 1988 and incorporated by reference herein. Another cytokine having this pathway is known as Natural Killer Cell Stimulatory Factor (NKSF), also termed Interleukin-12 (IL-12). This cytokine is described in detail in PCT patent application WO9205256, published Apr. 2, 1992 and incorporated by reference herein.

Still another cytokine sharing the IL-11 signal transduction pathway is Leukemia Inhibitory Factor (LIF), also known as Cholinergic Differentiation Factor (CDF), and is described in detail in PCT patent application WO90/02183, published Mar. 8, 1990, and incorporated by reference herein. Another cytokine characterized in this way is Oncostatin M (OSM), described in detail in European patent application No. 290,949, published Nov. 12, 1988 and incorporated by reference herein. Additionally, Ciliary Neurotrophic Factor (CNTF) shares this signal transduction pathway, and is anticipated to be useful in the methods of restoring these cell populations. CNTF is described in detail in PCT patent application WO9104316, published Apr. 4, 1991, and incorporated by reference herein.

It is further anticipated that other cytokines are likely to be useful in the methods of this invention, either in place of, or in combination with, IL-11 and/or one or more of the above disclosed cytokines. One additional cytokine useful in a therapeutic method or combination pharmaceutical preparation according to this invention is Interleukin-1 (IL-1). IL-1 is described in detail in European patent application No. 456,332, published Nov. 13, 1991, and incorporated by reference herein. Other cytokines which may be useful in these methods of restoring the cell populations selected from small intestinal epithelial cells, epithelial cells lining the large intestines and stomach, skin cells, hair cells, and sperm cells include Granulocyte Colony Stimulating Factor (G-CSF), Interleukin-3 (IL-3), Granulocyte-Macrophage Colony Stimulating Factor (GM-CSF) and Steel Factor (SCF). G-CSF is described in detail in PCT patent application WO9114776, published Oct. 3, 1991, and incorporated by reference herein. GM-CSF is described in detail in PCT patent application WO8600639, published Jan. 30, 1986, [see, also, European Patent Application No. 281,069, published Sep. 7, 1988] and incorporated by reference herein. IL-3 is described in detail in U.S. Pat. No. 4,959,455, issued Sep. 25, 1990, and incorporated by reference herein. SCF is described in detail in PCT patent application WO9105795, published May 2, 1991, and incorporated by reference herein.

For additional general information on these cytokines, see also, F. Takatsuki et al., *Cancer Res.*, 500:2885–2890 (1990); D. P. Gearing et al., *Science*, 255:1434–1437 (1992); G. Damia et al., *Cancer Res.*, 52:4082–4089 (1992).

For use in the methods of treatment disclosed in this invention, the above-described cytokines or biologically active fragments thereof may be prepared by genetic engineering techniques, as disclosed in the above-incorporated references. Moreover, in addition to recombinant techniques, the cytokine polypeptides described above may also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof which duplicate or partially duplicate the functionality thereof may also be used in the method of this invention. Thus, they may be employed as biologically active or immunological substitutes for the natural, purified cytokines useful in the present invention.

Modifications in the protein, peptide or DNA sequences of these cytokines or active fragments thereof may also produce proteins which may be employed in the methods of this invention. Such modified cytokines can be made by one skilled in the art using known techniques. Modifications of interest in the cytokine sequences, e.g., the IL-11 sequence, may include the replacement, insertion or deletion of one or more selected amino acid residues in the coding sequences. Mutagenic techniques for such replacement, insertion or deletion are well known to one skilled in the art. [See, e.g., U.S. Pat. No. 4,518,584.]

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present method, may also be easily made by one of skill in the art. One such modification may be the attachment of polyethylene glycol (PEG) onto existing lysine residues in the cytokine sequence or the insertion of one or more lysine residues or other amino acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions [Sambrook et al, Molecular Cloning. A Laboratory Manual., 2d edit., Cold Spring Harbor Laboratory, New York (1989)] will be similarly useful in this invention.

Also considered useful in these methods are fusion molecules, prepared by fusing the sequence or a biologically active fragment of the sequence of one cytokine to another cytokine or proteinaceous therapeutic agent, e.g., IL-11 fused to IL-6 [see, e.g., methods for fusion described in PCT Patent Application No. WO92/04455, published Mar. 19, 1992, incorporated herein by reference]. Alternatively, combinations of the cytokines may be administered together according to the method.

Thus, where in the description of the methods of this invention, a particular cytokine is mentioned by name, it is understood by those of skill in the art to encompass the protein produced by the sequences presently disclosed in the art, e.g., for IL-11, the sequences of FIG. 1 and FIG. 2, as well as proteins characterized by the modifications described above, yet which retain substantially similar activity in restoring the cell populations of one or more of the cell populations identified herein.

The present invention thus involves treating patients having damaged or depleted cell populations selected from small intestinal epithelial cells, epithelial cells lining the large intestines and stomach, liver epithelial cells, skin cells, hair cells, and sperm cells. The treatment involves administering an effective amount of a selected cytokine in a pharmaceutical carrier. This treatment enables the restoration or regeneration of the damaged or depleted cell population primarily by the stimulation, direct or indirect, of any undamaged stem cells. The stem cells are stimulated to differentiate into the cell population which had been damaged or depleted.

This invention is exemplified below in the treatment of small intestinal epithelial cells (gut cells) damaged by chemotherapy or radiation therapy with IL-11 as the selected cytokine. The effect of IL-11 on gut epithelial cells has been demonstrated by experiments, such as those illustrated in Example 2 below. For example, in studies with mice, IL-11 had a positive effect on mouse survival after exposure to 5-fluorouracil and irradiation without an effect on peripheral neutrophil (white blood cell) counts.

Where damage to, or depletion of, gut cells or other cell populations is caused by therapy, the treatment of the present invention may occur simultaneously with, or sequentially after, the therapy, e.g., chemotherapy or radiation. For example, effective amounts of IL-11 alone, another cytokine alone, or a combination of cytokines, may be administered in a suitable pharmaceutical carrier.

Preferably, treatment begins concurrently with or shortly after the chemotherapy or radiation therapy is begun and is continued until the level of the gut cells or other cells is returned to acceptable levels. However, the selected cytokine, e.g., IL-11, or combination of cytokines, may be administered for a suitable period of time prior to the beginning of chemotherapy or radiation therapy to improve the efficacy with which the cytokine, e.g., IL-11, stimulates the stem cell which differentiates into the mature gut cell.

The invention also involves methods for treating patients afflicted with damaged or depleted cell populations selected from small intestinal epithelial cells, epithelial cells lining the large intestines and stomach, liver epithelial cells, skin cells, hair cells, and sperm cells, where the damage or depletion is caused by autoimmune disease. For example, Crohn's disease, damages and depletes the population of normally rapidly dividing gut cells. Other autoimmune diseases may similarly affect the cells of the large intestine or stomach, liver, skin and hair, and sperm cells. The present invention also involves treating such conditions by administering effective doses of a selected cytokine, e.g., IL-11, or combination of cytokines.

Similarly, infection, trauma or shock can damage or deplete normal populations of gut cells, as well as the other cells mentioned herein, thereby requiring the administration of effective amounts of one or more cytokines, particularly IL-11.

In one embodiment of the present invention, a selected cytokine, IL-11, obtained by recombinant expression or prepared synthetically and purified to homogeneity, is combined with a pharmaceutical carrier suitable for internal administration. Purification is performed using conventional techniques (see, e.g., PCT/US90/06803 and the examples below).

Suitable pharmaceutically acceptable carriers facilitate administration of the cytokine, e.g., IL-11, and are well known in the art. Exemplary carriers include sterile saline, lactose, sucrose, calcium phosphate, gelatin, dextrin, agar, pectin, peanut oil, olive oil, sesame oil, and water. Additionally, the carrier or diluent includes a time delay material, such as glyceryl monostearate or glyceryl distearate alone or with a wax. In addition, slow release polymer formulations can be used. Suitable sustain-release matrices contain the active ingredient in a mixture with one or more of the following: sodium bentonite, ethylcellulose, stearic acid, calcium stearate, adipic acid, fumeric acid, polyethylene glycol, deacetylated chitin and cellulose acetate. Suitable preservatives and/or stabilizers may be included.

Alternatively, the selected cytokine, e.g., IL- 11, can be combined with other conventional agents useful in alleviating the symptoms associated with chemotherapy, such as antiemetics, anti-oxidants, and other hematopoietic growth factors.

The therapeutic method of the present invention may also include co-administration or combination of a selected cytokine with other human factors known to those of skill in the art. Exemplary cytokines or hematopoietins for such use include those cytokines specifically referenced above. Growth factors, such as B cell growth factor, B cell differentiation factor, or eosinophil differentiation factors may also prove useful in co-administration with these cytokines. Other agents for co-administration may include other pharmaceutically effective chemical agents and drugs, e.g., such as agents to control infection. The dosage recited below would be adjusted to compensate for such additional components in the therapeutic composition. Progress of the treated patient can be monitored by conventional methods.

Without wishing to be bound by theory, the inventors believe that treatment of damage to, or depletion of, the normally rapidly dividing gut epithelial cells with IL-11 or another cytokine, provides two important advantages to current methods of dealing with gut toxicity. First, the cytokine, e.g., IL-11, improves the integrity of the gut by stimulating the stem cells to restore a healthy cell population, thereby preventing entry of bacteria and fungi into the blood of the treated patient. IL-11 treatment of patients can thereby reduce the morbidity and mortality associated with chemotherapy and radiation treatment-induced gut damage. Additionally, IL-11 may allow increased amounts of chemotherapy and radiation therapy to be used in cancer treatments, a highly desirable effect, since this may improve the survival rates of patients with certain cancers which are currently fatal.

Similarly, in the treatment of autoimmune diseases of the small intestine, a cytokine, such as IL-11, is expected restore the cell population thereby improving healing and reducing morbidity and mortality without the deleterious side effects of previous therapies.

The treatment of a patient with a selected cytokine, such as IL-11, or combination of cytokines is anticipated to have the same effects on other cell populations, e.g., skin, hair, sperm cells, epithelial linings of stomach and large intestines, and liver epithelial cells, which are damaged or depleted by disease, infection, shock or trauma. The cytokine is theorized to restore healthy populations by stimulating stem cells into differentiating into mature cell populations.

In the treatment of any of these conditions resulting in damage to, or depletion of, the cell population, the cytokine, e.g., IL-11, can be administered by any suitable route, but is preferably administered systemically, i.e., parenterally. Of the parental routes, subcutaneous and intraperitoneal are preferred. With chemotherapy, intravenous administration may be desired.

A suitable treatment regimen for patients undergoing chemotherapy or radiation, or for patients who have already sustained cell damage or depletion due to trauma or disease, may be determined by the attending physician based upon such factors as the patient's age, sex, weight, and general health. Generally, a suitable dose of a cytokine, e.g., IL-11, ranges between about 1 µg and about 1000 mg or 50 to 5000 units. Another suitable dose may be in the range of between about 10 µg and about 1000 mg, and more preferably about 100 µg and about 500 mg, of cytokine, e.g., IL-11, per kg of body weight. A unit is conventionally described as the concentration of polypeptide which leads to half maximal stimulation in a suitable assay, e.g., for IL-11, the T1165 assay described in PCT/US90/06803.

These doses may be administered daily for between 1 day and 6 months, or for as long as is deemed necessary, depending on the nature of the cell damage or depletion.

When used to treat autoimmune conditions, the cytokine composition, e.g., IL-11, may be formulated to contain other agents useful in alleviating the symptoms of these conditions, including e.g., prednisone, cyclosporine, cyclophosphamide, and azathioprine, as well as other known agents.

Also, where treatment is directed to skin and hair cells, a pharmaceutical preparation may be prepared using agents which are conventional for topically administering therapeutics to the skin and hair, e.g., for systemic or local or topical administration. Suitable pharmaceutical carriers for a topical composition of the present invention may include several conventional ingredients of creams, lotions, gels or ointments. Such conventional ingredients are included in skin creams or oils for topical administration for treating a variety of diseases of the skin. Such compositions may be used as drug delivery systems to transmit the IL-11 through the skin or to facilitate the absorption of the IL-11 into the skin or onto a rash or other skin eruption. [See, e.g., U.S. Pat. No. 3,981,996; U.S. Pat. No. 4,731,241; U.S. Pat. No. 4,164,563; U.S. Pat. No. 3,924,004; U.S. Pat. No. 3,888,995; U.S. Pat. No. 3,592,930; and U.S. Pat. No. 4,753,958].

The following examples illustrate the methods of the present invention employing IL-11 as the selected cytokine, and gut cell populations damaged and depleted by chemotherapy as the model rapidly growing cell population. However, these examples do not limit the scope of the invention.

EXAMPLE 1

Human IL-11

The isolation and cloning of human IL-11 is described in detail in published PCT Application No. US90/06803 and now known to the art. The full sequence for human IL-11 was determined and is shown in FIG. 1. This protein is characterized by the sequence of FIG. 1 [SEQ ID NO:1 and 2]. These descriptions are incorporated by reference herein.

EXAMPLE 2

Thioredoxin-IL-11 Fusion Molecule

IL-11 was also prepared in a fusion molecule for use in the method of the present invention. The fusion molecule contained E. coli thioredoxin and recombinant IL-11, obtained as described in PCT Application No. US90/06803 incorporated by reference [see also Paul et al, Proc. Natl. Acad. Sci. U.S.A., 87:7512– 7516 (1990) and PCT Patent publication WO91/07495, published May 30, 1991 incorporated herein by reference].

The E. coli thioredoxin (trxA) gene was cloned based on its published sequence [Lim et al, J. Bacteriol., 163:311–316 (1985)] and employed to construct various related E. coli expression plasmids using standard DNA manipulation techniques, described extensively by Sambrook, Fritsch and Maniatis, Molecular Cloning. A Laboratory Manual, 2nd edition, Cold Spring Harbor Laboratory, Cold Spring Harbor, N.Y. (1989). (Nucleotides 2242–2568 of FIG. 2 encode the E. coli thioredoxin protein.)

An expression plasmid pALtrxA-781 was constructed containing the E. coli trxA gene without fusion to another sequence. This plasmid, which directs the accumulation of >10% of the total cell protein as thioredoxin in an E. coli host strain GI724, was further manipulated to provide for the construction of a trxA/IL-11 fusion sequence, resulting in the expression vector, pALtrxA/EK/IL-11ΔPro-581.

The entire sequence of the plasmid expression vector, pALtrxA/EK/IL-11ΔPro-581 (SEQ ID NO:3 and SEQ ID NO:4), is illustrated in FIG. 2 and contains the following principal features:

Nucleotides 1-2060 contain DNA sequences originating from the plasmid pUC-18 [Norrander et al, Gene, 26: 101-106 (1983)] including sequences containing the gene for β-lactamase which confers resistance to the antibiotic ampicillin in host E. coli strains, and a colE1-derived origin of replication. Nucleotides 2061- 2221 contain DNA sequences for the major leftward promoter (pL) of bacteriophage λ [Sanger et al, J. Mol. Biol., 162:729-773 (1982)], including three operator sequences, $O_L1$, $O_L2$ and $OL_3$. The operators are the binding sites for λcI repressor protein, intracellular levels of which control the amount of transcription initiation from pL. Nucleotides 2222-2241 contain a strong ribosome binding sequence derived from that of gene 10 of bacteriophage T7 [Dunn and Studier, J. Mol. Biol., 166:477-535 (1983)].

Nucleotides 2242-2568 contain a DNA sequence encoding the E. coli thioredoxin protein [Lim et al, J. Bacteriol., 163:311-316 (1985)]. There is no translation termination codon at the end of the thioredoxin coding sequence in this plasmid.

Nucleotides 2569-2583 contain DNA sequence encoding the amino acid sequence for a short, hydrophilic, flexible spacer peptide "--GSGSG--". Nucleotides 2584-2598 provide DNA sequence encoding the amino acid sequence for the cleavage recognition site of enterokinase (EC 3.4.4.8), "--DDDDK--" [Maroux et al, J. Biol. Chem., 246:5031-5039 (1971)].

Nucleotides 2599-3132 contain DNA sequence encoding the amino acid sequence of a modified form of mature human IL-11 [Paul et al, Proc. Natl. Acad. Sci. USA, 87:7512-7516 (1990)], the N-terminal prolyl-residue normally found in the natural protein has been deleted. Thus, these nucleotides encode IL-11 beginning with amino acid #2 of the mature native sequence. The sequence includes a translation termination codon at the 3'-end of the IL-11 sequence.

Nucleotides 3133-3159 provide a "Linker" DNA sequence containing restriction endonuclease sites. Nucleotides 3160-3232 provide a transcription termination sequence based on that of the E. coli aspA gene [Takagi et al, Nucl. Acids Res., 13:2063-2074 (1985)]. Nucleotides 3233-3632 are DNA sequences derived from pUC- 18.

As described in Example 3 below, when cultured under the appropriate conditions in a suitable E. coli host strain, this plasmid vector can direct the production of high levels (approximately 10% of the total cellular protein) of a thioredoxin-IL-11 fusion protein. By contrast, when not fused to thioredoxin, IL-11 accumulated to only 0.2% of the total cellular protein when expressed in an analogous host/vector system.

EXAMPLE 3

Expression of a Fusion Protein

A thioredoxin-IL-11 fusion protein was produced according to the following protocol using the plasmid constructed as described in Example 2. pALtrxA/EK/IL-11ΔPro-581 (SEQ ID NO: 3) was transformed into the E. coli host strain GI724 (F⁻, lacI$^q$, lacP$^{L8}$, ampC::λcI⁺) by the procedure of Dagert and Ehrlich, Gene, 6: 23 (1979). The untransformed host strain E. coli GI724 was deposited with the American Type Culture Collection, 12301 Parklawn Drive, Rockville, Md. on Jan. 31, 1991 under ATCC No. 55151 for patent purposes pursuant to applicable laws and regulations. Transformants were selected on 1.5% w/v agar plates containing IMC medium, which is composed of M9 medium [Miller, "Experiments in Molecular Genetics" Cold Spring Harbor Laboratory, New York (1972)] supplemented with 0.5% w/v glucose, 0.2% w/v casamino acids and 100 μg/ml ampicillin.

GI724 contains a copy of the wild-type λcI repressor gene stably integrated into the chromosome at the ampC locus, where it has been placed under the transcriptional control of Salmonella typhimurium trp promoter/operator sequences. In GI724, λcI protein is made only during growth in tryptophan-free media, such as minimal media or a minimal medium supplemented with casamino acids such as IMC, described above. Addition of tryptophan to a culture of GI724 will repress the trp promoter and turn off synthesis of λcI, gradually causing the induction of transcription from pL promoters if they are present in the cell.

GI724 transformed with pALtrxA/EK/IL-11ΔPro-581 (SEQ ID NO:3 and SEQ ID NO:4) was grown at 37° C. to an $A_{550}$ of 0.5 in IMC medium. Tryptophan was added to a final concentration of 100 μg/ml and the culture incubated for a further 4 hours. During this time thioredoxin-IL-11 fusion protein accumulated to approximately 10% of the total cell protein.

All of the fusion protein was found to be in the soluble cellular fraction, and was purified as follows. Cells were lysed in a French pressure cell at 20,000 psi in 50 mM HEPES pH 8.0, 1 mM phenylmethylsulfonyl fluoride. The lysate was clarified by centrifugation at 15,000× g for 30 minutes and the supernatant loaded onto a QAE-Toyopearl column. The flow-through fractions were discarded and the fusion protein eluted with 50 mM HEPES pH 8.0, 100 mM NaCl. The eluate was adjusted to 2M NaCl and loaded onto a column of phenyl-Toyopearl. The flow-through fractions were again discarded and the fusion protein eluted with 50 mM HEPES pH 8.0, 0.5 M NaCl.

The fusion protein was then dialyzed against 25 mM HEPES pH 8.0 and was >80% pure at this stage. By T1165 bioassay [Paul et al, cited above] the purified thioredoxin-IL-11 protein exhibited an activity of 8×10$^5$ U/mg. This value agrees closely on a molar basis with the activity of 2×10$^6$ U/mg found for COS cell-derived IL-11 in the same assay. One milligram of the fusion protein was cleaved at 37° C. for 20 hours with 1000 units of bovine enterokinase [Leipnieks and Light, J. Biol. Chem., 254:1677-1683 (1979)] in 1 ml 10mM Tris-Cl (pH8.0)/10 mM $CaCl_2$. IL-11 could be recovered from the reaction products by passing them over a QAE-Toyopearl column in 25 mM HEPES pH 8.0, where IL-11 was found in the flow-through fractions. Uncleaved fusion protein, thioredoxin and enterokinase remained bound on the column.

EXAMPLE 4

Treatment of Irradiated Mice

The IL-11 used in the tests below was obtained from Genetics Institute, Inc., Cambridge, Mass. and was prepared in *E. coli* essentially as described in the examples above. The IL-11 (140 μg/ml) was then mixed with 10 mM Tris buffer, to a pH of about 8.0. The level of endotoxin in this in vivo grade formulation is about 1.4 eu/mg of protein. The preparation also contains about 10% molar hydroxylmate and about 3 ng/ml (0.002%) thioredoxin.

Eight-ten week old C3H/HeJ (Jackson Labs) mice were administered intraperitoneally (i.p.) 150 mg/kg 5-fluorouracil (5-FU) diluted in Hanks Balanced Salt Solution (HBSS) containing 0.024 M Hepes buffer [both Gibco], three days prior to sublethal irradiation. Irradiation consisted of 6.0 Gys TBI delivered by Siemens 250 Kvp X-ray therapy machine, filtered with 1.0 mm Cu, giving half value layer of 2.1 mm Cu at 50 cm SSD, and with a dose rate of 78.13 (cGy/min). On the same day as the irradiation dose was given, mice were administered the above-described recombinant in vivo grade human IL-11 (Genetics Institute) at a divided dose (twice/day) of 250 micrograms/kg/day. These divided doses were given in 0.2 ml volumes subcutaneously in HBSS with Hepes and 0.1% bovine serum albumin (BSA; Boehringer-Mannheim). Control animals received the same volume of HBSS and BSA without IL-11. Treatment was continued for 9 to 18 days post-irradiation or until animals died.

Hematologic analysis of leukocyte cell counts and platelet counts were performed on tail vein bleeds on a Coulter Model ZM (Coulter Electronics) using a 100 micron aperture for leukocyte determinations and a 50 micron aperture for platelet determinations. Red blood cells were lysed using Zapglobin (Coulter) according to manufacturer's recommendations. Blood smears were stained with Wright-Giemsa using standard methods and examined at 100x for differential analysis. The absolute numbers of neutrophils, lymphocytes, monocytes, and eosinophils in the peripheral blood was calculated by multiplying the total leukocyte counts with the percentage of leukocytes obtained on the differential. Peripheral blood hematocrits were performed by spinning capillary tubes for five minutes in a Clay-Adams hematocrit centrifuge.

Whole dead mice (dying in the course of the experiment or by sacrifice) were fixed in 10% buffered formalin overnight. One femur/mouse was fixed in Bouin's solution. Tissues from each organ (liver, spleen, kidney, small intestine mesentery, abdominal wall, lung, heart, testes, and femur) were embedded in paraffin wax using standard techniques and four micron sections were cut and stained with hematoxylin and eosin. For analysis of small intestinal crypts, ten independent measurements of villus height, crypt depth, and metaphases/crypt were made in each section of small intestine using an objective-mounted micrometer.

Results are expressed in Table I below as the mean +/− SD unless otherwise stated. The probability of significant differences when two related groups were compared was determined using a two-tailed Student t-test. The probability of significant differences when multiple treatments were examined was determined by analysis of variance followed by Student-Newman-Keuls multiple range tests to define the unique subsets within the study.

TABLE I

Effect of IL-11 on Endogenous Infection Combined Modality Model

| Mouse No. | Day Post-Irradiat. Examined[1] | Diarrhea[2] | Hepatic Bacterial Foci | |
|---|---|---|---|---|
| | | | Macroscopic[3] | Microscopic[4] |
| BSA | | | | |
| 1 | 5 | + | 0 | +++ |
| 2 | 8 | − | 19 | ++ |
| 3 | 5 | + | 21 | +++ |
| 4 | 6 | − | 79 | +++ |
| 5 | 9 | − | 119 | +++ |
| IL-11 | | | | |
| 1 | 9 | + | 0 | + |
| 2 | 4 | + | 0 | − |
| 3 | 9 | − | 14 | ++ |
| 4 | 9 | − | 3 | + |
| 5 | 9 | − | 0 | − |

[1] All animals sacrificed at day 9, other days represent day of death.
[2] + = present at day of death
− = no diarrhea
[3] Surface foci present on fixed liver.
[4] Microscopic foci present on examination of randomly chosen histologic sections; + < 10 foci/section; ++ 10–50; +++ > 50.

In three separate experiments, all control mice died between day 3 and day 10 after irradiation, while only 3/13 (23%) of IL-11 treated mice died (on days 4, 9, 10 post-irradiation). In experiment 1, all control animals died by day 9. Animals were autopsied on the day of death or (in the treated group) on day 9 by sacrificing remaining animals (day of examination listed in Table I. At autopsy, 4/5 mice in the control group had macroscopic infection foci in the liver compared to 2/5 of the IL-11 treated mice. In addition, the foci present in IL-11 treated mice were present in fewer numbers and smaller in size (Table I). These foci subsequently were demonstrated to contain *E. coli* bacteria by identification using microbiological analysis. Microscopically many foci (12–129/random section) were found within the liver from control mice, while fewer (6–21/section) were demonstrated in IL-11 treated mice (Table I). Similar bacterial foci were also seen in the mesentery and spleen of animals.

Surprisingly, these differences in mortality and the presence of bacterial foci in organs of mice were not associated with differences in peripheral leukocyte counts or absolute neutrophil counts as shown by data in Table II.

TABLE II

| | Effect of rhIL-11 on Peripheral Blood Counts in Mice Combined Modality Model | | |
|---|---|---|---|
| Day[1] | Treatment | WBC × $10^3$/mm$^3$ | Platelet $10^3$/mm$^3$ |
| Day 1 | BSA | 5.56 ± 1.80(5) | 894.7 ± 168.3(5) |
| | IL-11 | 4.89 ± 0.16(5) | 770.3 ± 192.6(5) |
| Day 3 | BSA | 0.49 ± 0.16(10) | 294.8 ± 43.1(10) |
| | IL-11 | 0.64 ± 0.31(10) | 454.1 ± 115.5(10) |
| Day 4 | BSA | 0.43 ± 0.04(10) | 237.4 ± 109.6(10) |
| | IL-11 | 0.49 ± 0.14(10) | 337.3 ± 143.2(10) |
| Day 5 | BSA | 0.30 ± 0.06(9) | 126.6 ± 55.1(10) |
| | IL-11 | 0.31 ± 0.07(11) | 171.9 ± 76.9(11) |
| Day 6 | BSA | 0.40 ± 0.24(9) | 134.4 ± 80.7(9) |
| | IL-11 | 0.47 ± 0.22(12) | 257.9 ± 195.2(12) |
| Day 8 | BSA | 1.19 ± 0.13(2) | 236.1 ± 18.2(2) |
| | IL-11 | 0.72 ± 0.23(7) | 365.6 ± 256.1(7) |
| Day 9 | BSA | 1.39 ± 0.32(2) | 269.0 ± 100.8(2) |
| | IL-11 | 1.06 ± 0.45(9) | 248.8 ± 92.4(9) |

[1] Post-irradiation
( ) number of animals
\* $p < 0.001$ compared to BSA group

Since *E. coli* are a known resident organism of the small intestine, the increase in bacterial infection and mortality in the control animals probably reflects gut toxicity from irradiation and chemotherapy. Histologic section of the small intestine and morphometric quantitation of the length of the small intestine villi confirmed extensive damage in control mice as shown by data in Table III. In contrast, IL-11 treatment was associated with almost complete preservation of villi length (Table III). In addition, IL-11 treated mice demonstrated near normal numbers of mitotic crypt cells, a further indication of stimulation of proliferation of crypt progenitor or stem cells.

TABLE III

| | Effect of IL-11 of Murine Gut Epithelium Combined Modality Mode | | | | | |
|---|---|---|---|---|---|---|
| | C | V | C | Crypt | Mitoses/ | Mitoses/ |
| | Crypt Depth[1] | Villi Length | C + V × 100% | Cir. | Crypt | 100μ crypt |
| Normal (2) Day 5 | 84.1 ± 21.1 | 477.7 ± 99.8 | 15.4 ± 5.9 | 162.3 ± 11.6 | 1.8 ± 0.4 | 1.07 ± 0.14 |
| BSA(5) Day 9 | 122.8 ± 29.5 | 253.7 ± 79.7 | 33.5 ± 8.2 | 853.4 ± 62.2 | 0.9 ± 0.4 | 0.10 ± 0.04 |
| IL-11(5) | 117.1 ± 14.5 | 512.8 ± 6.7** | 19.5 ± 6.7** | 928.2 ± 104.4 | 2.0 ± 0.5* | 0.22 ± 0.06* |
| BSA(2) | 124.6 ± 40.7 | 330.1 ± 92.1 | 27.3 ± 1.0 | 830.0 ± 28.2 | 1.1 ± 0 | 0.13 ± 0 |
| IL-11(2) | 98.5 ± 7.0 | 405.9 ± 84.3 | 19.9 ± 4.4 | 957.5 ± 10.4 | 2.2 ± 0.6 | 0.23 ± 0.06 |

( ) number of animals
[1] = in microns
\* = $< 0.01$ compared to BSA group
\*\* = $< 0.02$ compared to BSA group These data demonstrate that the administration of IL-11 in vivo has marked positive effects on the recovery of small intestinal crypt epithelial cells from the combined cytotoxic effects of radiation and chemotherapy.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for maintaining a gut epithelial cell population comprising the step of administering to a patient a pharmacologically effective amount of a cytokine selected from the group consisting of interleukin-11, interleukin-6, leukemia inhibitory factor, oncostatin M, and ciliary neurotrophic factor.

2. The method of claim 1, further comprising administering an additional cytokine.

3. A method for maintaining a gut epithelial cell population comprising the step of administering to a patient a pharmacologically effective amount of IL-11.

4. A method for maintaining a gut epithelial cell population comprising the step of administering to a patient a pharmacologically effective amount of IL-6.

5. A method for maintaining a small intestinal epithelial cell population comprising the step of administering to a patient a pharmaceutically effective amount of a cytokine selected from the group consisting of interleukin-11, interleukin-6, leukemia inhibitory factor, oncostatin M, and ciliary neurotrophic factor.

6. The method of claim 5, further comprising administering an additional cytokine.

7. A method for maintaining a small intestinal epithelial cell population comprising the step of administering to a patient a pharmaceutically effective amount of IL-11.

8. A method for maintaining a small intestinal epithelial cell population comprising the step of administering to a patient a pharmaceutically effective amount of IL-6.

9. A method for maintaining a large intestinal epithelial cell population comprising the step of administering to a patient a pharmaceutically effective amount of a cytokine selected from the group consisting of interleukin-11, interleukin-6, leukemia inhibitory factor, oncostatin M, and ciliary neurotrophic factor.

10. The method of claim 9, further comprising administering an additional cytokine.

11. A method for maintaining a large intestinal epithelial cell population comprising the step of administering to a patient a pharmaceutically effective amount of IL-11.

12. A method for maintaining a large intestinal epithelial cell population comprising the step of administering to a patient a pharmaceutically effective amount of IL-6.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 977 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 70..666

( x i ) SEQUENCE DESCRIPTION: SEQ ID NO:1:

```
AGCTGGGAAG GGTTAAAGGC CCCCGGCTCC CTGCCCCCTG CCCTGGGGAA CCCCTGGCCC        60

TGCGGGGAC ATG AAC TGT GTT TGC CGC CTG GTC CTG GTC GTG CTG AGC          108
          Met Asn Cys Val Cys Arg Leu Val Leu Val Val Leu Ser
           1               5                  10

CTG TGG CCA GAT ACA GCT GTC GCC CCT GGG CCA CCA CCT GGC CCC CCT        156
Leu Trp Pro Asp Thr Ala Val Ala Pro Gly Pro Pro Pro Gly Pro Pro
     15              20                  25

CGA GTT TCC CCA GAC CCT CGG GCC GAG CTG GAC AGC ACC GTG CTC CTG        204
Arg Val Ser Pro Asp Pro Arg Ala Glu Leu Asp Ser Thr Val Leu Leu
 30              35                  40                      45

ACC CGC TCT CTC CTG GCG GAC ACG CGG CAG CTG GCT GCA CAG CTG AGG        252
Thr Arg Ser Leu Leu Ala Asp Thr Arg Gln Leu Ala Ala Gln Leu Arg
             50                  55                  60

GAC AAA TTC CCA GCT GAC GGG GAC CAC AAC CTG GAT TCC CTG CCC ACC        300
Asp Lys Phe Pro Ala Asp Gly Asp His Asn Leu Asp Ser Leu Pro Thr
             65                  70                  75

CTG GCC ATG AGT GCG GGG GCA CTG GGA GCT CTA CAG CTC CCA GGT GTG        348
Leu Ala Met Ser Ala Gly Ala Leu Gly Ala Leu Gln Leu Pro Gly Val
             80                  85                  90

CTG ACA AGG CTG CGA GCG GAC CTA CTG TCC TAC CTG CGG CAC GTG CAG        396
Leu Thr Arg Leu Arg Ala Asp Leu Leu Ser Tyr Leu Arg His Val Gln
         95                 100                 105

TGG CTG CGC CGG GCA GGT GGC TCT TCC CTG AAG ACC CTG GAG CCC GAG        444
Trp Leu Arg Arg Ala Gly Gly Ser Ser Leu Lys Thr Leu Glu Pro Glu
110             115                 120                     125

CTG GGC ACC CTG CAG GCC CGA CTG GAC CGG CTG CTG CGC CGG CTG CAG        492
Leu Gly Thr Leu Gln Ala Arg Leu Asp Arg Leu Leu Arg Arg Leu Gln
                130                 135                 140

CTC CTG ATG TCC CGC CTG GCC CTG CCC CAG CCA CCC CCG GAC CCG CCG        540
Leu Leu Met Ser Arg Leu Ala Leu Pro Gln Pro Pro Pro Asp Pro Pro
            145                 150                 155

GCG CCC CCG CTG GCG CCC CCC TCC TCA GCC TGG GGG GGC ATC AGG GCC        588
Ala Pro Pro Leu Ala Pro Pro Ser Ser Ala Trp Gly Gly Ile Arg Ala
            160                 165                 170

GCC CAC GCC ATC CTG GGG GGG CTG CAC CTG ACA CTT GAC TGG GCC GTG        636
Ala His Ala Ile Leu Gly Gly Leu His Leu Thr Leu Asp Trp Ala Val
    175                 180                 185

AGG GGA CTG CTG CTG CTG AAG ACT CGG CTG TGACCCGAGG CCCAGAGCCA          686
Arg Gly Leu Leu Leu Leu Lys Thr Arg Leu
190                 195

CCACCGTCCT TCCAAAGCCA CATCTTATTT ATTTATTTAT TTCGGTACTG GGGGCGAAAC      746
```

-continued

```
AGCCAGGTGA TCCCCCTGCC TTTAGCTCCC CCTAGTTAGA GACAGTCCTT CCGTGAGGCT    806
GGGGGGCATC TGTGCCTTAT TTATACTTAT TTATTTCAGG AGCGGGGTG GGCTCCTGGG    866
TCCCCGAGGA GGAGGGAGCT GGGGTCCCGG ATTCTTGTGT CCACAGACTT CTGCCCTGGC    926
TCCTCCCCCT CGAGGCCTGG GCAGGAATAC ATACTATTTA TTTAAGAGCT C             977
```

( 2 ) INFORMATION FOR SEQ ID NO:2:

( i ) SEQUENCE CHARACTERISTICS:
    ( A ) LENGTH: 199 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Asn Cys Val Cys Arg Leu Val Leu Val Val Leu Ser Leu Trp Pro
  1               5                  10                  15
Asp Thr Ala Val Ala Pro Gly Pro Pro Gly Pro Pro Arg Val Ser
             20                  25                  30
Pro Asp Pro Arg Ala Glu Leu Asp Ser Thr Val Leu Leu Thr Arg Ser
             35                  40                  45
Leu Leu Ala Asp Thr Arg Gln Leu Ala Ala Gln Leu Arg Asp Lys Phe
 50                  55                  60
Pro Ala Asp Gly Asp His Asn Leu Asp Ser Leu Pro Thr Leu Ala Met
 65                  70                  75                  80
Ser Ala Gly Ala Leu Gly Ala Leu Gln Leu Pro Gly Val Leu Thr Arg
             85                  90                  95
Leu Arg Ala Asp Leu Leu Ser Tyr Leu Arg His Val Gln Trp Leu Arg
            100                 105                 110
Arg Ala Gly Gly Ser Ser Leu Lys Thr Leu Glu Pro Glu Leu Gly Thr
            115                 120                 125
Leu Gln Ala Arg Leu Asp Arg Leu Leu Arg Arg Leu Gln Leu Leu Met
            130                 135                 140
Ser Arg Leu Ala Leu Pro Gln Pro Pro Asp Pro Pro Ala Pro Pro
145                 150                 155                 160
Leu Ala Pro Pro Ser Ser Ala Trp Gly Gly Ile Arg Ala Ala His Ala
            165                 170                 175
Ile Leu Gly Gly Leu His Leu Thr Leu Asp Trp Ala Val Arg Gly Leu
            180                 185                 190
Leu Leu Leu Lys Thr Arg Leu
            195
```

( 2 ) INFORMATION FOR SEQ ID NO:3:

( i ) SEQUENCE CHARACTERISTICS:
    ( A ) LENGTH: 3632 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 2242..3132

( i x ) FEATURE:
    ( A ) NAME/KEY: misc_feature
    ( B ) LOCATION: 2242..2568
    ( D ) OTHER INFORMATION: /product="E. coli thioredoxin

```
                    protein"
              / note="Lim et al., J. Bacteriol., 163:311-316
                    (1985)"

( i x ) FEATURE:
          ( A ) NAME/KEY: RBS
          ( B ) LOCATION: 2222..2241
          ( D ) OTHER INFORMATION: /standard_name="ribosome binding
                    sequence"
              / note="Dunn and Studier, J. Mol. Biol.,
                    166:477-535 (1983)"

( i x ) FEATURE:
          ( A ) NAME/KEY: misc_feature
          ( B ) LOCATION: 2061..2221
          ( D ) OTHER INFORMATION: /function="leftward promoter of
                    bacteriophage lambda"
              / note="Sanger et al., J. Mol. Biol., 162:729-773
                    (1982)"

( i x ) FEATURE:
          ( A ) NAME/KEY: misc_feature
          ( B ) LOCATION: 1..2060
          ( D ) OTHER INFORMATION: /function="derived from plasmid
                    pUC-18"
              / note="Norrander et al., Gene, 26:101-106 (1983)"

( i x ) FEATURE:
          ( A ) NAME/KEY: misc_feature
          ( B ) LOCATION: 2569..2583
          ( D ) OTHER INFORMATION: /function="short, hydrophilic
                    flexible spacer peptide"

( i x ) FEATURE:
          ( A ) NAME/KEY: misc_feature
          ( B ) LOCATION: 2584..2598
          ( D ) OTHER INFORMATION: /function="enterokinase cleavage
                    recognition site"
              / note="Maroux et al., J. Biol. Chem.,
                    246:5031-5039 (1971)"

( i x ) FEATURE:
          ( A ) NAME/KEY: misc_feature
          ( B ) LOCATION: 2599..3132
          ( D ) OTHER INFORMATION: /product="modified form of mature
                    human IL11"
              / note="Paul et al., Proc. Natl. Acad. Sci. USA,
                    87:7512-7516 (1990)"

( i x ) FEATURE:
          ( A ) NAME/KEY: misc_feature
          ( B ) LOCATION: 3133..3159
          ( D ) OTHER INFORMATION: /function="linker sequence
                    containing restriction endonuclease sites"

( i x ) FEATURE:
          ( A ) NAME/KEY: misc_feature
          ( B ) LOCATION: 3160..3232
          ( D ) OTHER INFORMATION: /function="transcription
                    termination sequence based on E. coli aspA"
              / note="Takagi et al., Nucl. Acids Res.,
                    13:2063-2074 (1985)"

( i x ) FEATURE:
          ( A ) NAME/KEY: misc_feature
          ( B ) LOCATION: 3233..3632
          ( D ) OTHER INFORMATION: /function="DNA sequences derived
                    from pUC-18"

( x i ) SEQUENCE DESCRIPTION: SEQ ID NO:3:

GACGAAAGGG CCTCGTGATA CGCCTATTTT TATAGGTTAA TGTCATGATA ATAATGGTTT      60
CTTAGACGTC AGGTGGCACT TTTCGGGGAA ATGTGCGCGG AACCCCTATT TGTTTATTTT     120
TCTAAATACA TTCAAATATG TATCCGCTCA TGAGACAATA ACCCTGATAA ATGCTTCAAT     180
AATATTGAAA AAGGAAGAGT ATGAGTATTC AACATTTCCG TGTCGCCCTT ATTCCCTTTT     240
```

-continued

```
TTGCGGCATT TTGCCTTCCT GTTTTTGCTC ACCCAGAAAC GCTGGTGAAA GTAAAAGATG    300
CTGAAGATCA GTTGGGTGCA CGAGTGGGTT ACATCGAACT GGATCTCAAC AGCGGTAAGA    360
TCCTTGAGAG TTTTCGCCCC GAAGAACGTT TTCCAATGAT GAGCACTTTT AAAGTTCTGC    420
TATGTGGCGC GGTATTATCC CGTATTGACG CCGGGCAAGA GCAACTCGGT CGCCGCATAC    480
ACTATTCTCA GAATGACTTG GTTGAGTACT CACCAGTCAC AGAAAAGCAT CTTACGGATG    540
GCATGACAGT AAGAGAATTA TGCAGTGCTG CCATAACCAT GAGTGATAAC ACTGCGGCCA    600
ACTTACTTCT GACAACGATC GGAGGACCGA AGGAGCTAAC CGCTTTTTTG CACAACATGG    660
GGGATCATGT AACTCGCCTT GATCGTTGGG AACCGGAGCT GAATGAAGCC ATACCAAACG    720
ACGAGCGTGA CACCACGATG CCTGTAGCAA TGGCAACAAC GTTGCGCAAA CTATTAACTG    780
GCGAACTACT TACTCTAGCT TCCCGGCAAC AATTAATAGA CTGGATGGAG GCGGATAAAG    840
TTGCAGGACC ACTTCTGCGC TCGGCCCTTC CGGCTGGCTG GTTTATTGCT GATAAATCTG    900
GAGCCGGTGA GCGTGGGTCT CGCGGTATCA TTGCAGCACT GGGGCCAGAT GGTAAGCCCT    960
CCCGTATCGT AGTTATCTAC ACGACGGGGA GTCAGGCAAC TATGGATGAA CGAAATAGAC   1020
AGATCGCTGA GATAGGTGCC TCACTGATTA AGCATTGGTA ACTGTCAGAC CAAGTTTACT   1080
CATATATACT TTAGATTGAT TTAAAACTTC ATTTTTAATT TAAAAGGATC TAGGTGAAGA   1140
TCCTTTTTGA TAATCTCATG ACCAAAATCC CTTAACGTGA GTTTTCGTTC CACTGAGCGT   1200
CAGACCCCGT AGAAAAGATC AAAGGATCTT CTTGAGATCC TTTTTTTCTG CGCGTAATCT   1260
GCTGCTTGCA AACAAAAAAA CCACCGCTAC CAGCGGTGGT TTGTTTGCCG GATCAAGAGC   1320
TACCAACTCT TTTTCCGAAG GTAACTGGCT TCAGCAGAGC GCAGATACCA AATACTGTCC   1380
TTCTAGTGTA GCCGTAGTTA GGCCACCACT TCAAGAACTC TGTAGCACCG CCTACATACC   1440
TCGCTCTGCT AATCCTGTTA CCAGTGGCTG CTGCCAGTGG CGATAAGTCG TGTCTTACCG   1500
GGTTGGACTC AAGACGATAG TTACCGGATA AGGCGCAGCG GTCGGGCTGA ACGGGGGGTT   1560
CGTGCACACA GCCCAGCTTG GAGCGAACGA CCTACACCGA ACTGAGATAC CTACAGCGTG   1620
AGCATTGAGA AAGCGCCACG CTTCCCGAAG GGAGAAAGGC GGACAGGTAT CCGGTAAGCG   1680
GCAGGGTCGG AACAGGAGAG CGCACGAGGG AGCTTCCAGG GGGAAACGCC TGGTATCTTT   1740
ATAGTCCTGT CGGGTTTCGC CACCTCTGAC TTGAGCGTCG ATTTTTGTGA TGCTCGTCAG   1800
GGGGGCGGAG CCTATGGAAA AACGCCAGCA ACGCGGCCTT TTTACGGTTC CTGGCCTTTT   1860
GCTGGCCTTT TGCTCACATG TTCTTTCCTG CGTTATCCCC TGATTCTGTG GATAACCGTA   1920
TTACCGCCTT TGAGTGAGCT GATACCGCTC GCCGCAGCCG AACGACCGAG CGCAGCGAGT   1980
CAGTGAGCGA GGAAGCGGAA GAGCGCCCAA TACGCAAACC GCCTCTCCCC GCGCGTTGGC   2040
CGATTCATTA ATGCAGAATT GATCTCTCAC CTACCAAACA ATGCCCCCT GCAAAAAATA   2100
AATTCATATA AAAAACATAC AGATAACCAT CTGCGGTGAT AAATTATCTC TGGCGGTGTT   2160
GACATAAATA CCACTGGCGG TGATACTGAG CACATCAGCA GGACGCACTG ACCACCATGA   2220
ATTCAAGAAG GAGATATACA T ATG AGC GAT AAA ATT ATT CAC CTG ACT GAC    2271
             Met Ser Asp Lys Ile Ile His Leu Thr Asp
               1             5                 10
GAC AGT TTT GAC ACG GAT GTA CTC AAA GCG GAC GGG GCG ATC CTC GTC    2319
Asp Ser Phe Asp Thr Asp Val Leu Lys Ala Asp Gly Ala Ile Leu Val
           15                  20                  25
GAT TTC TGG GCA GAG TGG TGC GGT CCG TGC AAA ATG ATC GCC CCG ATT    2367
Asp Phe Trp Ala Glu Trp Cys Gly Pro Cys Lys Met Ile Ala Pro Ile
         30                  35                  40
CTG GAT GAA ATC GCT GAC GAA TAT CAG GGC AAA CTG ACC GTT GCA AAA    2415
```

```
              Leu  Asp  Glu  Ile  Ala  Asp  Glu  Tyr  Gln  Gly  Lys  Leu  Thr  Val  Ala  Lys
                         45                       50                       55

CTG  AAC  ATC  GAT  CAA  AAC  CCT  GGC  ACT  GCG  CCG  AAA  TAT  GGC  ATC  CGT                2463
Leu  Asn  Ile  Asp  Gln  Asn  Pro  Gly  Thr  Ala  Pro  Lys  Tyr  Gly  Ile  Arg
     60                       65                       70

GGT  ATC  CCG  ACT  CTG  CTG  CTG  TTC  AAA  AAC  GGT  GAA  GTG  GCG  GCA  ACC                2511
Gly  Ile  Pro  Thr  Leu  Leu  Leu  Phe  Lys  Asn  Gly  Glu  Val  Ala  Ala  Thr
75                        80                        85                        90

AAA  GTG  GGT  GCA  CTG  TCT  AAA  GGT  CAG  TTG  AAA  GAG  TTC  CTC  GAC  GCT                2559
Lys  Val  Gly  Ala  Leu  Ser  Lys  Gly  Gln  Leu  Lys  Glu  Phe  Leu  Asp  Ala
                         95                       100                      105

AAC  CTG  GCC  GGT  TCT  GGT  TCT  GGT  GAT  GAC  GAT  GAC  AAA  GGT  CCA  CCA                2607
Asn  Leu  Ala  Gly  Ser  Gly  Ser  Gly  Asp  Asp  Asp  Asp  Lys  Gly  Pro  Pro
                    110                      115                      120

CCA  GGT  CCA  CCT  CGA  GTT  TCC  CCA  GAC  CCT  CGG  GCC  GAG  CTG  GAC  AGC                2655
Pro  Gly  Pro  Pro  Arg  Val  Ser  Pro  Asp  Pro  Arg  Ala  Glu  Leu  Asp  Ser
          125                      130                      135

ACC  GTG  CTC  CTG  ACC  CGC  TCT  CTC  CTG  GCG  GAC  ACG  CGG  CAG  CTG  GCT                2703
Thr  Val  Leu  Leu  Thr  Arg  Ser  Leu  Leu  Ala  Asp  Thr  Arg  Gln  Leu  Ala
     140                      145                      150

GCA  CAG  CTG  AGG  GAC  AAA  TTC  CCA  GCT  GAC  GGG  GAC  CAC  AAC  CTG  GAT                2751
Ala  Gln  Leu  Arg  Asp  Lys  Phe  Pro  Ala  Asp  Gly  Asp  His  Asn  Leu  Asp
155                      160                      165                      170

TCC  CTG  CCC  ACC  CTG  GCC  ATG  AGT  GCG  GGG  GCA  CTG  GGA  GCT  CTA  CAG                2799
Ser  Leu  Pro  Thr  Leu  Ala  Met  Ser  Ala  Gly  Ala  Leu  Gly  Ala  Leu  Gln
                    175                      180                      185

CTC  CCA  GGT  GTG  CTG  ACA  AGG  CTG  CGA  GCG  GAC  CTA  CTG  TCC  TAC  CTG                2847
Leu  Pro  Gly  Val  Leu  Thr  Arg  Leu  Arg  Ala  Asp  Leu  Leu  Ser  Tyr  Leu
               190                      195                      200

CGG  CAC  GTG  CAG  TGG  CTG  CGC  CGG  GCA  GGT  GGC  TCT  TCC  CTG  AAG  ACC                2895
Arg  His  Val  Gln  Trp  Leu  Arg  Arg  Ala  Gly  Gly  Ser  Ser  Leu  Lys  Thr
          205                      210                      215

CTG  GAG  CCC  GAG  CTG  GGC  ACC  CTG  CAG  GCC  CGA  CTG  GAC  CGG  CTG  CTG                2943
Leu  Glu  Pro  Glu  Leu  Gly  Thr  Leu  Gln  Ala  Arg  Leu  Asp  Arg  Leu  Leu
     220                      225                      230

CGC  CGG  CTG  CAG  CTC  CTG  ATG  TCC  CGC  CTG  GCC  CTG  CCC  CAG  CCA  CCC                2991
Arg  Arg  Leu  Gln  Leu  Leu  Met  Ser  Arg  Leu  Ala  Leu  Pro  Gln  Pro  Pro
235                      240                      245                      250

CCG  GAC  CCG  CCG  GCG  CCC  CCG  CTG  GCG  CCC  CCC  TCC  TCA  GCC  TGG  GGG                3039
Pro  Asp  Pro  Pro  Ala  Pro  Pro  Leu  Ala  Pro  Pro  Ser  Ser  Ala  Trp  Gly
                    255                      260                      265

GGC  ATC  AGG  GCC  GCC  CAC  GCC  ATC  CTG  GGG  GGG  CTG  CAC  CTG  ACA  CTT                3087
Gly  Ile  Arg  Ala  Ala  His  Ala  Ile  Leu  Gly  Gly  Leu  His  Leu  Thr  Leu
          270                      275                      280

GAC  TGG  GCC  GTG  AGG  GGA  CTG  CTG  CTG  CTG  AAG  ACT  CGG  CTG  TGAAAGCTTA              3139
Asp  Trp  Ala  Val  Arg  Gly  Leu  Leu  Leu  Leu  Lys  Thr  Arg  Leu
     285                      290                      295

TCGATACCGT  CGACCTGCAG  TAATCGTACA  GGGTAGTACA  AATAAAAAAG  GCACGTCAGA                         3199

TGACGTGCCT  TTTTTCTTGT  GAGCAGTAAG  CTTGGCACTG  GCCGTCGTTT  TACAACGTCG                         3259

TGACTGGGAA  AACCCTGGCG  TTACCCAACT  TAATCGCCTT  GCAGCACATC  CCCCTTTCGC                         3319

CAGCTGGCGT  AATAGCGAAG  AGGCCCGCAC  CGATCGCCCT  TCCCAACAGT  TGCGCAGCCT                         3379

GAATGGCGAA  TGGCGCCTGA  TGCGGTATTT  TCTCCTTACG  CATCTGTGCG  GTATTTCACA                         3439

CCGCATATAT  GGTGCACTCT  CAGTACAATC  TGCTCTGATG  CCGCATAGTT  AAGCCAGCCC                         3499

CGACACCCGC  CAACACCCGC  TGACGCGCCC  TGACGGGCTT  GTCTGCTCCC  GGCATCCGCT                         3559

TACAGACAAG  CTGTGACCGT  CTCCGGGAGC  TGCATGTGTC  AGAGGTTTTC  ACCGTCATCA                         3619
```

```
CCGAAACGCG CGA                                                                    3632
```

( 2 ) INFORMATION FOR SEQ ID NO:4:

( i ) SEQUENCE CHARACTERISTICS:
        ( A ) LENGTH: 296 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Asp Lys Ile Ile His Leu Thr Asp Asp Ser Phe Asp Thr Asp
 1               5                  10                  15
Val Leu Lys Ala Asp Gly Ala Ile Leu Val Asp Phe Trp Ala Glu Trp
                20                  25                  30
Cys Gly Pro Cys Lys Met Ile Ala Pro Ile Leu Asp Glu Ile Ala Asp
                35                  40                  45
Glu Tyr Gln Gly Lys Leu Thr Val Ala Lys Leu Asn Ile Asp Gln Asn
        50                  55                  60
Pro Gly Thr Ala Pro Lys Tyr Gly Ile Arg Gly Ile Pro Thr Leu Leu
 65                  70                  75                  80
Leu Phe Lys Asn Gly Glu Val Ala Ala Thr Lys Val Gly Ala Leu Ser
                85                  90                  95
Lys Gly Gln Leu Lys Glu Phe Leu Asp Ala Asn Leu Ala Gly Ser Gly
                100                 105                 110
Ser Gly Asp Asp Asp Asp Lys Gly Pro Pro Gly Pro Pro Arg Val
                115                 120                 125
Ser Pro Asp Pro Arg Ala Glu Leu Asp Ser Thr Val Leu Leu Thr Arg
 130                 135                 140
Ser Leu Leu Ala Asp Thr Arg Gln Leu Ala Ala Gln Leu Arg Asp Lys
 145                 150                 155                 160
Phe Pro Ala Asp Gly Asp His Asn Leu Asp Ser Leu Pro Thr Leu Ala
                165                 170                 175
Met Ser Ala Gly Ala Leu Gly Ala Leu Gln Leu Pro Gly Val Leu Thr
                180                 185                 190
Arg Leu Arg Ala Asp Leu Leu Ser Tyr Leu Arg His Val Gln Trp Leu
                195                 200                 205
Arg Arg Ala Gly Gly Ser Ser Leu Lys Thr Leu Glu Pro Glu Leu Gly
 210                 215                 220
Thr Leu Gln Ala Arg Leu Asp Arg Leu Leu Arg Arg Leu Gln Leu Leu
 225                 230                 235                 240
Met Ser Arg Leu Ala Leu Pro Gln Pro Pro Asp Pro Pro Ala Pro
                245                 250                 255
Pro Leu Ala Pro Pro Ser Ser Ala Trp Gly Gly Ile Arg Ala Ala His
                260                 265                 270
Ala Ile Leu Gly Gly Leu His Leu Thr Leu Asp Trp Ala Val Arg Gly
                275                 280                 285
Leu Leu Leu Leu Lys Thr Arg Leu
                290                 295
```